United States Patent
Runquist et al.

(10) Patent No.: US 11,471,571 B2
(45) Date of Patent: Oct. 18, 2022

(54) NEGATIVE PRESSURE WOUND THERAPY CANISTERS

(71) Applicant: Smith & Nephew, Inc., Memphis, TN (US)

(72) Inventors: Lars Runquist, Minneapolis, MN (US); Evan Leingang, Minneapolis, MN (US); Richard A. Thompson, II, Minneapolis, MN (US); Thom Tedham, Minneapolis, MN (US)

(73) Assignee: Smith & Nephew, Inc., Memphis, TN (US)

( * ) Notice: Subject to any disclaimer, the term of this patent is extended or adjusted under 35 U.S.C. 154(b) by 337 days.

(21) Appl. No.: 16/606,179

(22) PCT Filed: Apr. 17, 2018

(86) PCT No.: PCT/US2018/028004
§ 371 (c)(1),
(2) Date: Oct. 17, 2019

(87) PCT Pub. No.: WO2018/195101
PCT Pub. Date: Oct. 25, 2018

(65) Prior Publication Data
US 2020/0046887 A1 Feb. 13, 2020

Related U.S. Application Data

(60) Provisional application No. 62/487,249, filed on Apr. 19, 2017, provisional application No. 62/563,004, filed on Sep. 25, 2017.

(51) Int. Cl.
*A61M 1/00* (2006.01)
*A61F 13/00* (2006.01)
(Continued)

(52) U.S. Cl.
CPC ..... *A61M 1/0001* (2013.01); *A61F 13/00068* (2013.01); *A61M 1/784* (2021.05);
(Continued)

(58) Field of Classification Search
CPC combination set(s) only.
See application file for complete search history.

(56) References Cited

U.S. PATENT DOCUMENTS

| 730,062 A | 6/1903 | Widmer |
| 2,468,445 A | 4/1949 | Kenneth et al. |

(Continued)

FOREIGN PATENT DOCUMENTS

| CN | 2623320 Y | 7/2004 |
| DE | 4312852 A1 | 10/1993 |

(Continued)

OTHER PUBLICATIONS

International Search Report and Written Opinion, re PCT Application No. PCT/US2018/028004, dated Aug. 31, 2018.
(Continued)

*Primary Examiner* — Tatyana Zalukaeva
*Assistant Examiner* — Ilya Y Treyger
(74) *Attorney, Agent, or Firm* — Knobbe, Martens, Olson & Bear LLP

(57) ABSTRACT

Embodiments of a canister for a negative pressure wound therapy systems and methods for operating the systems are disclosed. In some embodiments, the canister includes a receptacle for receiving wound exudate. A filter stack is interposed between the receptacle and the pump assembly and provides a fluid flow path therebetween. The flow path is more easily navigable by gas than by liquid, thereby allowing the pump assembly to apply a negative pressure to the canister without aspirating wound exudate into filters housed within the filter stack.

24 Claims, 25 Drawing Sheets

(51) Int. Cl.
  *A61M 27/00* (2006.01)
  *A61F 13/02* (2006.01)
  *A61B 17/50* (2006.01)
(52) U.S. Cl.
  CPC ....... *A61M 1/86* (2021.05); *A61M 2205/7518* (2013.01); *A61M 2205/7527* (2013.01); *A61M 2205/7536* (2013.01)

(56) References Cited

U.S. PATENT DOCUMENTS

| | | |
|---|---|---|
| 3,980,166 A | 9/1976 | De Feudis |
| 4,063,556 A | 12/1977 | Thomas et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,321,020 A | 3/1982 | Mittal |
| 4,331,147 A | 5/1982 | Armstrong |
| 4,569,674 A | 2/1986 | Phillips et al. |
| 4,578,060 A | 3/1986 | Huck et al. |
| 4,585,397 A | 4/1986 | Crawford et al. |
| 4,604,313 A | 8/1986 | McFarland et al. |
| 4,758,238 A | 7/1988 | Sundblom et al. |
| 4,767,417 A | 8/1988 | Boehringer et al. |
| 4,826,494 A | 5/1989 | Richmond et al. |
| 4,832,299 A | 5/1989 | Gorton et al. |
| 4,865,816 A | 9/1989 | Walz et al. |
| 4,870,975 A | 10/1989 | Cronk et al. |
| 4,979,944 A | 12/1990 | Luzsicza |
| 4,988,344 A | 1/1991 | Reising et al. |
| 4,988,345 A | 1/1991 | Reising |
| 5,071,104 A | 12/1991 | Witt et al. |
| 5,135,485 A | 8/1992 | Cohen et al. |
| 5,141,504 A | 8/1992 | Herweck et al. |
| 5,156,602 A | 10/1992 | Steffler |
| 5,219,428 A | 6/1993 | Stern |
| 5,246,353 A | 9/1993 | Sohn |
| D352,463 S | 11/1994 | Kubo |
| 5,360,445 A | 11/1994 | Goldowsky |
| 5,386,735 A | 2/1995 | Langdon |
| 5,397,299 A | 3/1995 | Karwoski et al. |
| 5,411,474 A | 5/1995 | Ott et al. |
| 5,458,586 A | 10/1995 | Adiletta |
| 5,466,229 A | 11/1995 | Elson et al. |
| 5,484,428 A | 1/1996 | Drainville et al. |
| 5,591,297 A | 1/1997 | Ahr |
| 5,630,855 A | 5/1997 | Lundb Ack |
| 5,685,214 A | 11/1997 | Neff et al. |
| 5,707,173 A | 1/1998 | Cottone et al. |
| 5,785,700 A | 7/1998 | Olson |
| 5,787,928 A | 8/1998 | Allen et al. |
| 5,807,359 A | 9/1998 | Bemis et al. |
| D400,249 S | 10/1998 | Holubar |
| 5,876,387 A | 3/1999 | Killian et al. |
| 5,882,743 A | 3/1999 | McConnell |
| D408,625 S | 4/1999 | Barker |
| 5,960,837 A | 10/1999 | Cude |
| 6,010,527 A | 1/2000 | Augustine et al. |
| 6,075,177 A | 6/2000 | Bahia et al. |
| 6,099,493 A | 8/2000 | Swisher |
| 6,102,205 A | 8/2000 | Greff et al. |
| 6,168,758 B1 | 1/2001 | Forsberg et al. |
| D449,891 S | 10/2001 | Moro |
| 6,352,233 B1 | 3/2002 | Barberich |
| D456,514 S | 4/2002 | Brown et al. |
| 6,395,955 B1 | 5/2002 | Roe et al. |
| 6,458,109 B1 | 10/2002 | Henley et al. |
| 6,468,199 B1 | 10/2002 | Satou et al. |
| 6,501,002 B1 | 12/2002 | Roe et al. |
| 6,547,255 B1 | 4/2003 | Donaway et al. |
| D475,132 S | 5/2003 | Randolph |
| 6,575,333 B1 | 6/2003 | Raboin |
| D477,869 S | 7/2003 | Vijfvinkel |
| D478,659 S | 8/2003 | Hall et al. |
| 6,620,379 B1 | 9/2003 | Piuk et al. |
| D481,459 S | 10/2003 | Nahm |
| 6,723,430 B2 | 4/2004 | Kurata et al. |
| 6,755,807 B2 | 6/2004 | Risk, Jr. et al. |
| 6,764,462 B2 | 7/2004 | Risk, Jr. et al. |
| 6,800,074 B2 | 10/2004 | Henley et al. |
| 6,820,483 B1 | 11/2004 | Beckerman |
| 6,856,821 B2 | 2/2005 | Johnson |
| 6,885,116 B2 | 4/2005 | Knirck et al. |
| D504,953 S | 5/2005 | Ryan |
| D516,217 S | 2/2006 | Brown et al. |
| 7,004,915 B2 | 2/2006 | Boynton et al. |
| D522,657 S | 6/2006 | Murphy et al. |
| 7,066,949 B2 | 6/2006 | Gammons et al. |
| 7,153,294 B1 | 12/2006 | Farrow |
| D537,944 S | 3/2007 | Eda et al. |
| 7,198,046 B1 | 4/2007 | Argenta et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| D565,177 S | 3/2008 | Locke et al. |
| 7,367,342 B2 | 5/2008 | Butler |
| 7,438,705 B2 | 10/2008 | Karpowicz et al. |
| D580,285 S | 11/2008 | Hendrickson et al. |
| D581,042 S | 11/2008 | Randolph et al. |
| D581,522 S | 11/2008 | Randolph et al. |
| D585,137 S | 1/2009 | Onoda et al. |
| 7,503,910 B2 | 3/2009 | Adahan |
| D590,934 S | 4/2009 | Randolph et al. |
| 7,524,315 B2 | 4/2009 | Blott et al. |
| D593,676 S | 6/2009 | Locke et al. |
| D594,114 S | 6/2009 | Locke et al. |
| 7,569,742 B2 | 8/2009 | Haggstrom et al. |
| 7,604,610 B2 | 10/2009 | Shener et al. |
| 7,608,066 B2 | 10/2009 | Vogel |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,758,555 B2 | 7/2010 | Kelch et al. |
| 7,794,450 B2 | 9/2010 | Blott et al. |
| D625,801 S | 10/2010 | Pidgeon et al. |
| 7,837,673 B2 | 11/2010 | Vogel |
| D630,313 S | 1/2011 | Pidgeon et al. |
| D630,725 S | 1/2011 | Pidgeon et al. |
| D635,588 S | 4/2011 | Sprules |
| 7,927,318 B2 | 4/2011 | Risk, Jr. et al. |
| 7,976,598 B2 | 7/2011 | Matula et al. |
| D644,250 S | 8/2011 | Barber et al. |
| 7,998,125 B2 | 8/2011 | Weston |
| 8,021,348 B2 | 9/2011 | Risk, Jr. et al. |
| 8,048,046 B2 | 11/2011 | Hudspeth et al. |
| D650,894 S | 12/2011 | Gonzalez |
| 8,162,909 B2 | 4/2012 | Blott et al. |
| 8,172,817 B2 | 5/2012 | Michaels et al. |
| 8,240,470 B2 | 8/2012 | Pidgeon et al. |
| 8,257,327 B2 | 9/2012 | Blott et al. |
| 8,267,909 B2 | 9/2012 | Clementi et al. |
| 8,294,586 B2 | 10/2012 | Pidgeon et al. |
| 8,303,555 B2 | 11/2012 | Miau et al. |
| 8,323,264 B2 | 12/2012 | Weston et al. |
| 8,333,744 B2 | 12/2012 | Hartwell et al. |
| 8,348,910 B2 | 1/2013 | Blott et al. |
| D675,728 S | 2/2013 | Tout et al. |
| 8,372,049 B2 | 2/2013 | Jaeb et al. |
| 8,403,902 B2 | 3/2013 | Locke et al. |
| D681,806 S | 5/2013 | Kataoka et al. |
| 8,439,882 B2 | 5/2013 | Kelch |
| 8,444,392 B2 | 5/2013 | Turner et al. |
| 8,480,641 B2 | 7/2013 | Jacobs |
| 8,494,349 B2 | 7/2013 | Gordon |
| 8,568,386 B2 | 10/2013 | Malhi |
| 8,641,693 B2 | 2/2014 | Locke et al. |

(56) References Cited

U.S. PATENT DOCUMENTS

| | | |
|---|---|---|
| 8,652,111 B2 | 2/2014 | Pratt et al. |
| 8,668,677 B2 | 3/2014 | Eckstein et al. |
| 8,814,840 B2 | 8/2014 | Evans et al. |
| 8,814,841 B2 | 8/2014 | Hartwell |
| 8,858,517 B2 | 10/2014 | Pan et al. |
| 8,974,429 B2 | 3/2015 | Gordon et al. |
| 9,019,681 B2 | 4/2015 | Locke et al. |
| 9,084,845 B2 | 7/2015 | Adie et al. |
| 9,155,821 B2 | 10/2015 | Wudyka |
| 9,211,486 B2 | 12/2015 | Locke et al. |
| D750,222 S | 2/2016 | Chang |
| 9,320,838 B2 | 4/2016 | Hartwell et al. |
| 9,327,063 B2 | 5/2016 | Locke et al. |
| D764,653 S | 8/2016 | Bjelovuk et al. |
| 9,408,954 B2 | 8/2016 | Gordon et al. |
| D772,924 S | 11/2016 | Begin et al. |
| 9,526,817 B2 | 12/2016 | Blott et al. |
| 9,561,312 B2 | 2/2017 | Heaton et al. |
| 9,636,440 B2 | 5/2017 | Weston et al. |
| D788,911 S | 6/2017 | Deutsch et al. |
| 9,669,139 B2 | 6/2017 | Coulthard et al. |
| 9,775,935 B2 | 10/2017 | Weston et al. |
| D802,744 S | 11/2017 | Bjelovuk et al. |
| D814,016 S | 3/2018 | Bjelovuk et al. |
| D815,726 S | 4/2018 | Bjelovuk et al. |
| 10,004,835 B2 | 6/2018 | Wiesner |
| D835,648 S | 12/2018 | Begin et al. |
| 10,155,070 B2 | 12/2018 | Childress et al. |
| 10,207,031 B2 | 2/2019 | Toth |
| 10,328,188 B2 | 6/2019 | Deutsch et al. |
| D870,265 S | 12/2019 | Bjelovuk et al. |
| 10,556,045 B2 | 2/2020 | Carr et al. |
| 10,617,800 B2 | 4/2020 | Middleton et al. |
| 10,617,801 B2 | 4/2020 | Vernon-Harcourt et al. |
| D891,607 S | 7/2020 | Bjelovuk et al. |
| 10,898,621 B2 | 1/2021 | Chen et al. |
| 10,905,806 B2 | 2/2021 | Armstrong et al. |
| 2002/0145012 A1 | 10/2002 | Ho |
| 2003/0101826 A1 | 6/2003 | Neubert |
| 2003/0163101 A1 | 8/2003 | Say |
| 2003/0181850 A1 | 9/2003 | Diamond et al. |
| 2003/0212357 A1 | 11/2003 | Pace |
| 2003/0235635 A1 | 12/2003 | Fong et al. |
| 2004/0006321 A1 | 1/2004 | Cheng et al. |
| 2004/0087918 A1 | 5/2004 | Johnson, III et al. |
| 2004/0153029 A1 | 8/2004 | Blischak et al. |
| 2004/0167482 A1 | 8/2004 | Watson |
| 2004/0180093 A1 | 9/2004 | Burton et al. |
| 2004/0233631 A1 | 11/2004 | Lord |
| 2005/0144711 A1 | 7/2005 | Valadez et al. |
| 2005/0166683 A1 | 8/2005 | Krivitski et al. |
| 2005/0248045 A1 | 11/2005 | Anthony |
| 2006/0059980 A1 | 3/2006 | Matsubara et al. |
| 2006/0129137 A1 | 6/2006 | Lockwood et al. |
| 2006/0280650 A1 | 12/2006 | Wong et al. |
| 2007/0021697 A1 | 1/2007 | Ginther et al. |
| 2007/0055209 A1 | 3/2007 | Patel et al. |
| 2007/0118096 A1 | 5/2007 | Smith et al. |
| 2007/0135779 A1 | 6/2007 | Lalomia et al. |
| 2007/0219535 A1 | 9/2007 | Phung et al. |
| 2008/0011667 A1 | 1/2008 | Ruschke |
| 2008/0033400 A1 | 2/2008 | Holper et al. |
| 2008/0125698 A1 | 5/2008 | Gerg et al. |
| 2008/0183233 A1 | 7/2008 | Koch et al. |
| 2008/0281281 A1 | 11/2008 | Meyer et al. |
| 2009/0099519 A1 | 4/2009 | Kaplan |
| 2009/0157016 A1 | 6/2009 | Adahan |
| 2009/0204049 A1 | 8/2009 | Lee |
| 2009/0240218 A1 | 9/2009 | Braga et al. |
| 2009/0254066 A1 | 10/2009 | Heaton et al. |
| 2009/0299251 A1 | 12/2009 | Buan |
| 2009/0299306 A1 | 12/2009 | Buan |
| 2009/0312725 A1 | 12/2009 | Braga |
| 2010/0022990 A1 | 1/2010 | Karpowicz et al. |
| 2010/0030132 A1 | 2/2010 | Niezgoda et al. |
| 2010/0036333 A1 | 2/2010 | Schenk, III et al. |
| 2010/0049150 A1 | 2/2010 | Braga et al. |
| 2010/0318043 A1 | 12/2010 | Malhi et al. |
| 2010/0318071 A1 | 12/2010 | Wudyka |
| 2011/0038741 A1 | 2/2011 | Lissner et al. |
| 2011/0066110 A1 | 3/2011 | Fathallah et al. |
| 2011/0077605 A1 | 3/2011 | Karpowicz et al. |
| 2011/0106027 A1 | 5/2011 | Vess et al. |
| 2011/0112493 A1 | 5/2011 | Koch et al. |
| 2011/0130712 A1 | 6/2011 | Topaz |
| 2011/0152799 A1 | 6/2011 | Bendele et al. |
| 2011/0313375 A1 | 12/2011 | Michaels |
| 2012/0000478 A1 | 1/2012 | Wagenhals |
| 2012/0035560 A1 | 2/2012 | Eddy et al. |
| 2012/0046624 A1 | 2/2012 | Locke et al. |
| 2012/0123323 A1 | 5/2012 | Kagan et al. |
| 2012/0123358 A1 | 5/2012 | Hall et al. |
| 2012/0181405 A1 | 7/2012 | Zlatic et al. |
| 2012/0271256 A1 | 10/2012 | Locke et al. |
| 2013/0144227 A1 | 6/2013 | Locke et al. |
| 2013/0144235 A1 | 6/2013 | Augustine et al. |
| 2014/0074053 A1 | 3/2014 | Locke et al. |
| 2014/0128822 A1 | 5/2014 | Malhi |
| 2014/0207091 A1 | 7/2014 | Heagle et al. |
| 2014/0276494 A1 | 9/2014 | Cisko et al. |
| 2014/0320283 A1 | 10/2014 | Lawhorn |
| 2016/0184498 A1 | 6/2016 | Jaeb et al. |
| 2016/0287765 A1 | 10/2016 | Canner et al. |
| 2017/0165405 A1 | 6/2017 | Muser et al. |
| 2018/0028728 A1 | 2/2018 | Aarestad et al. |
| 2018/0304065 A1 | 10/2018 | Armstrong et al. |
| 2018/0333521 A1 | 11/2018 | Hudspeth et al. |
| 2018/0353352 A1 | 12/2018 | Fink et al. |
| 2019/0009008 A1 | 1/2019 | Hartwell |
| 2019/0060532 A1 | 2/2019 | Hartwell et al. |
| 2019/0099527 A1 | 4/2019 | Schuessler et al. |
| 2020/0171217 A9 | 6/2020 | Braga et al. |

FOREIGN PATENT DOCUMENTS

| | | |
|---|---|---|
| DE | 102010036405 A1 | 1/2012 |
| EP | 0358302 A2 | 3/1990 |
| EP | 2223711 A1 | 9/2010 |
| EP | 2248546 A2 | 11/2010 |
| GB | 1415096 A | 11/1975 |
| GB | 2418738 A | 4/2006 |
| JP | 2000202022 A | 7/2000 |
| WO | WO-8700439 A1 | 1/1987 |
| WO | WO-03022333 A1 | 3/2003 |
| WO | WO-03053346 A2 | 7/2003 |
| WO | WO-2007087808 A1 | 8/2007 |
| WO | WO-2007087809 A1 | 8/2007 |
| WO | WO-2008036344 A1 | 3/2008 |
| WO | WO-2009077722 A1 | 6/2009 |
| WO | WO-2009086580 A1 | 7/2009 |
| WO | WO-2013126049 A1 | 8/2013 |
| WO | WO-2015091070 A1 | 6/2015 |

OTHER PUBLICATIONS

Fong K.D., et al., "SNaP Wound Care System: Ultraportable Mechanically Powered Negative Pressure Wound Therapy," Advances in Wound Care, vol. 1(1), Feb. 2012, 4 pages.

Huntleigh Healthcare, "Negative Pressure Positive Outcomes," WoundASSIST TNP Console and Canister Brochure, 2007, 6 pages.

International Preliminary Report on Patentability for Application No. PCT/US2018/028004, dated Oct. 31, 2019, 14 pages.

Invitation to Pay Additional Fees and, Where Applicable, Protest Fee for Application No. PCT/US2018/028004, dated Jul. 10, 2018, 19 pages.

KCI, "V.A.C. Freedom User's Guide," May 2002, 16 pages.

Piaggesi A., et al., "SNAP® Wound Care System Made Easy," Wounds International, retrieved from URL: http://www.woundsinternational.com, vol. 3 (1), Feb. 2012, 6 pages.

The Free Dictionary, "Evaporation," The American Heritage®, Science Dictionary, 2005, 3 pages.

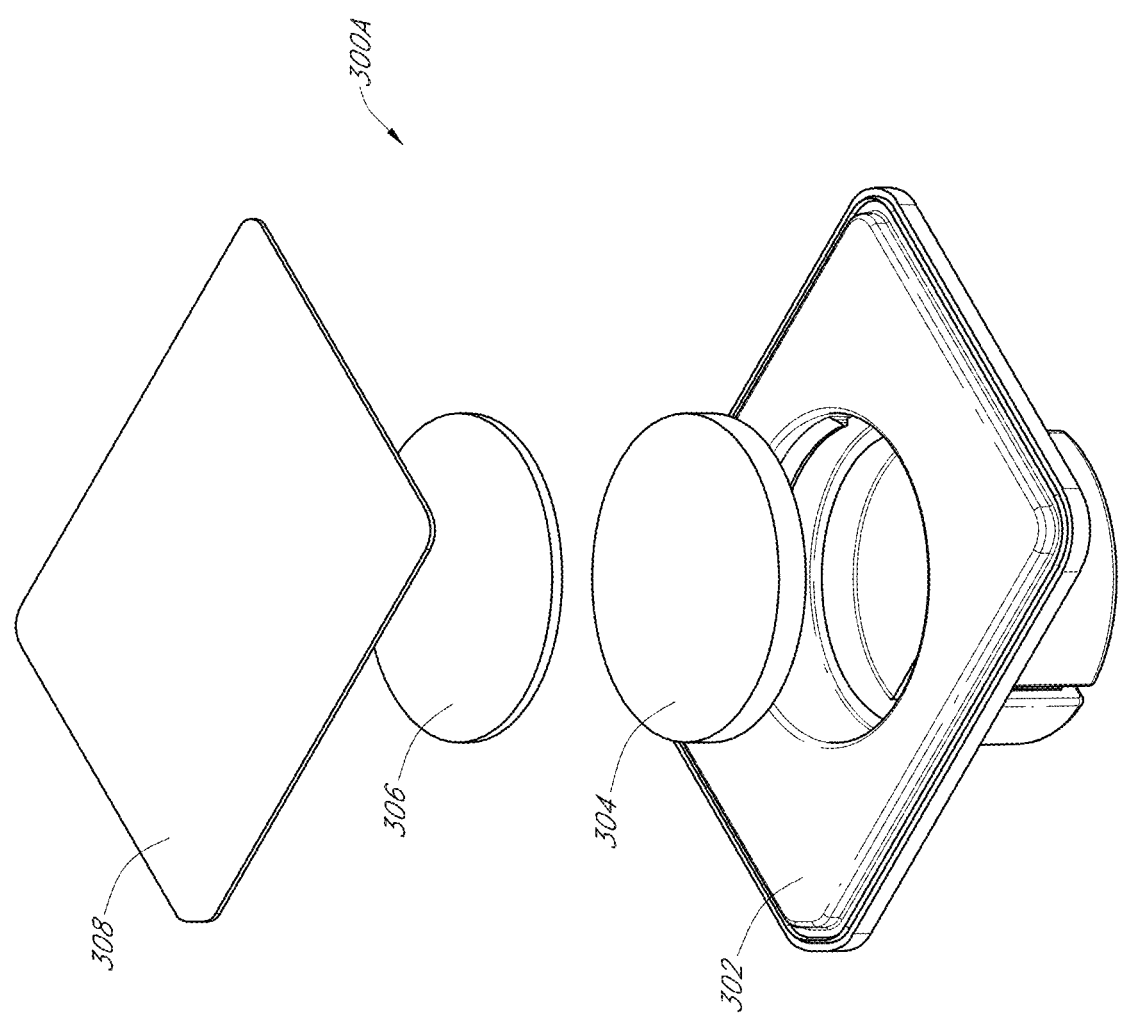

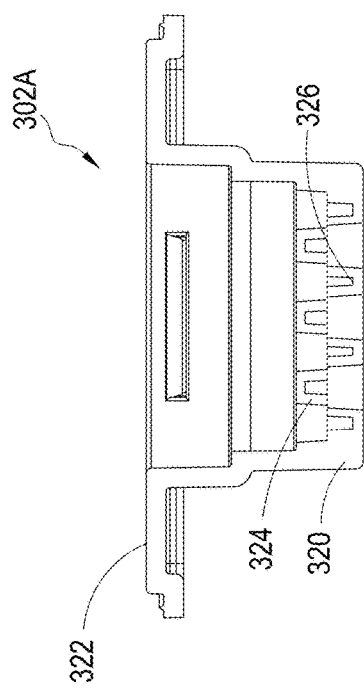
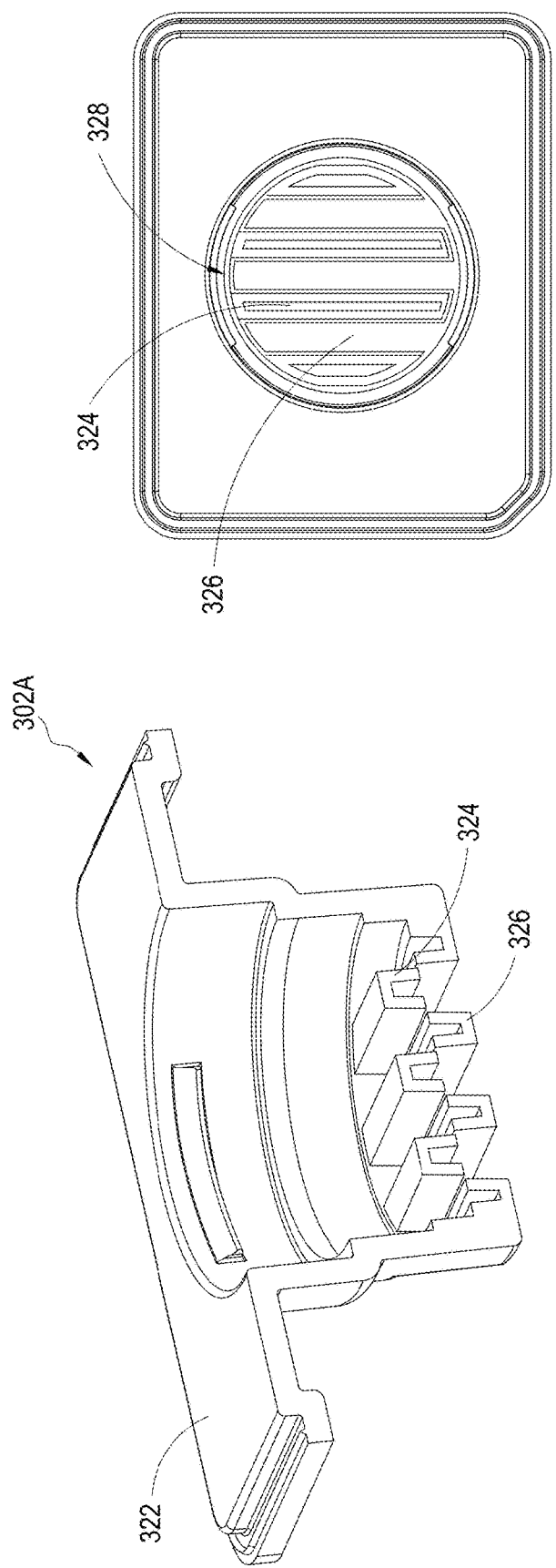

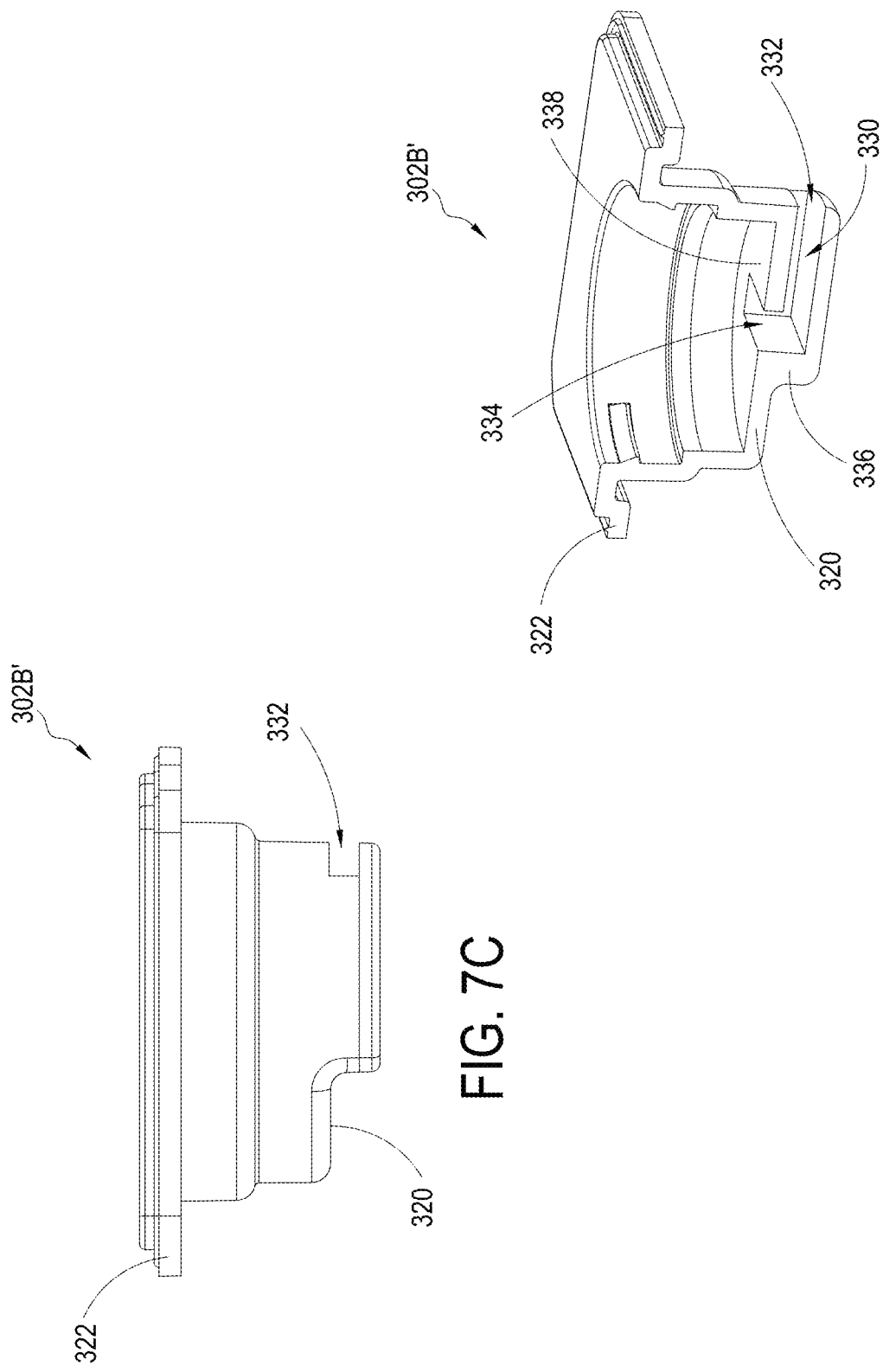

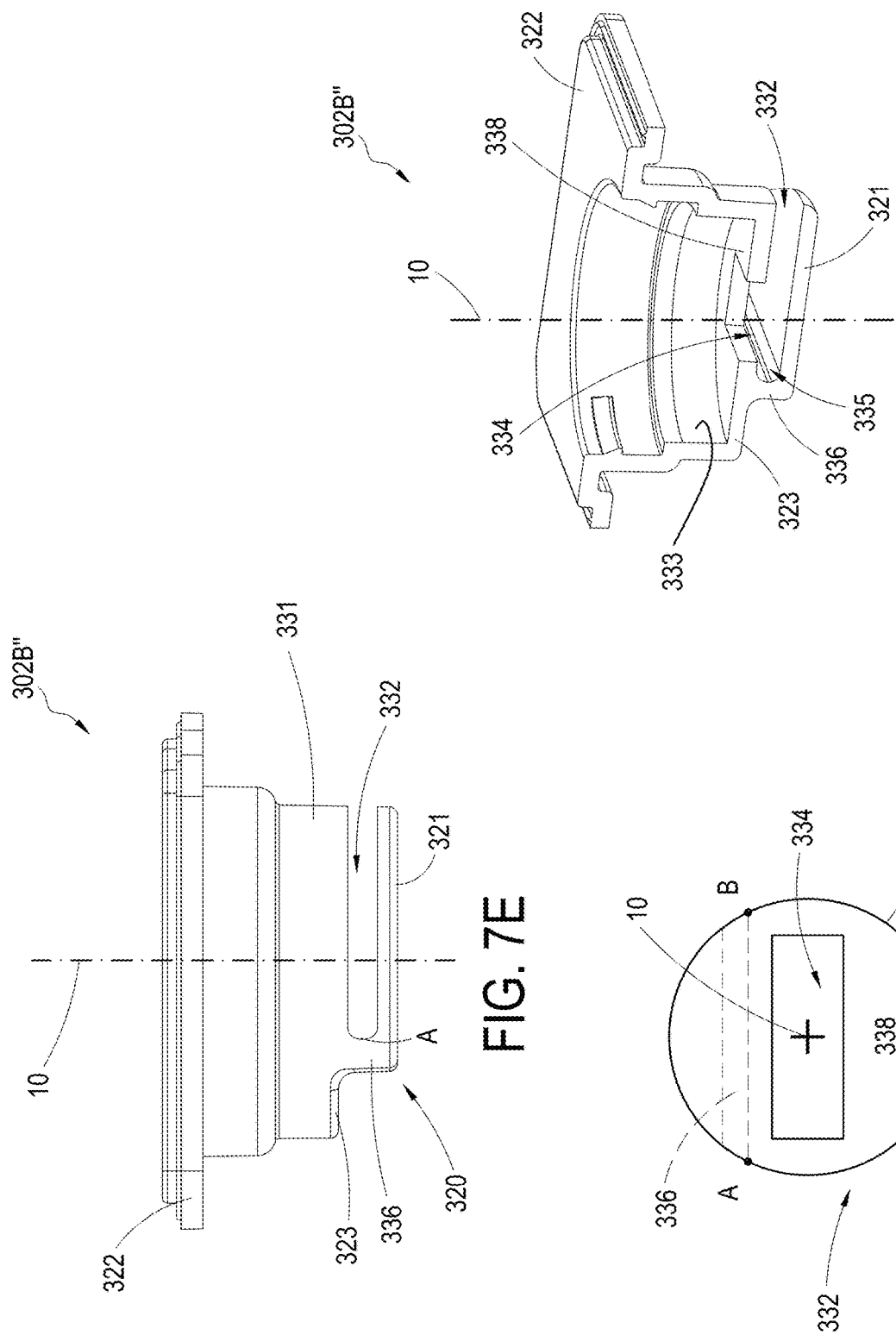
FIG. 7E
FIG. 7F
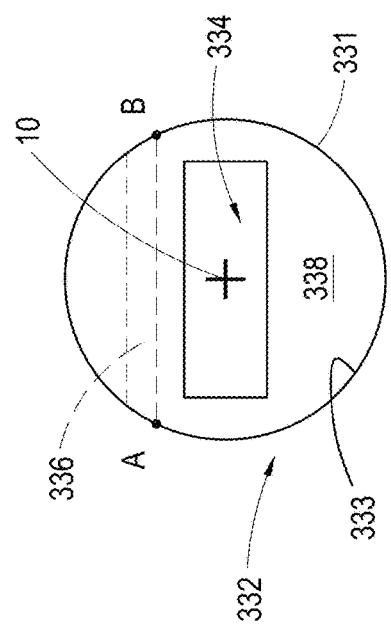
FIG. 7G

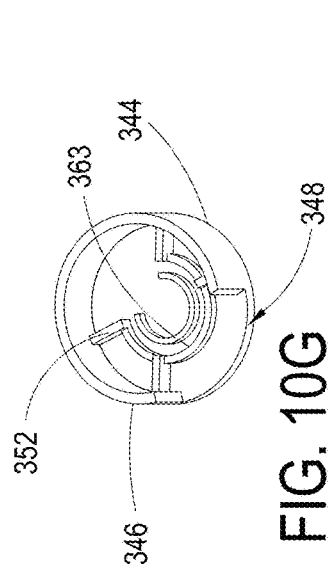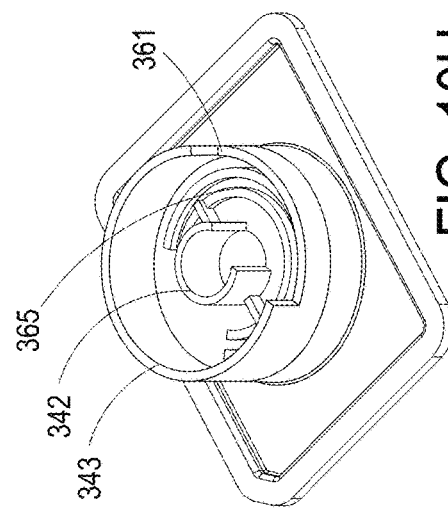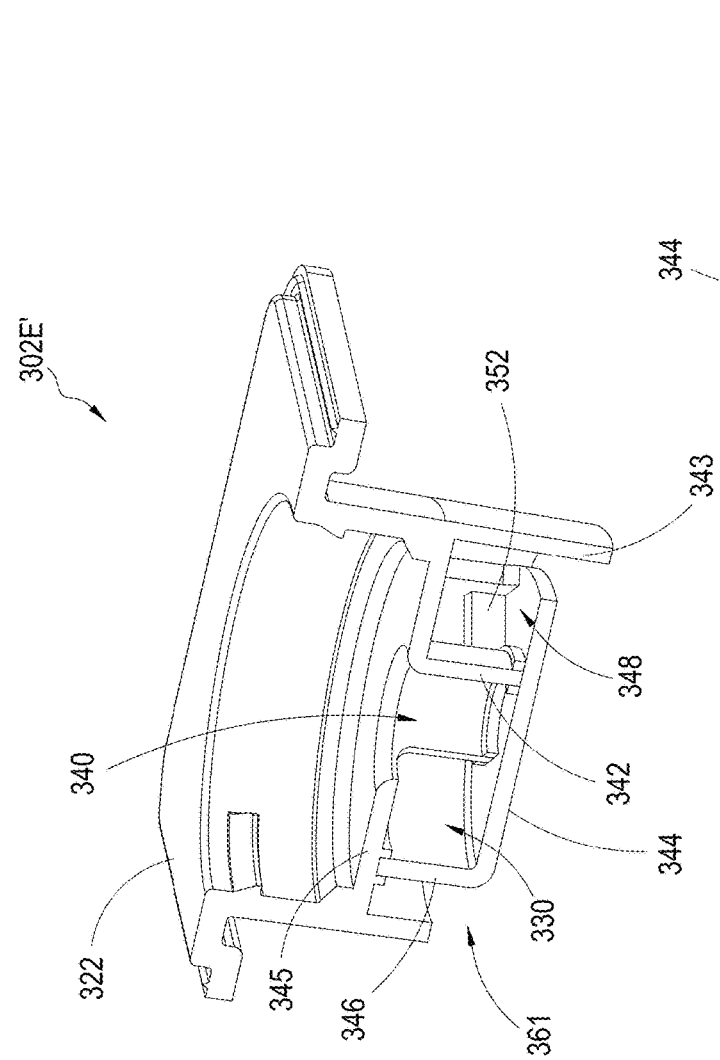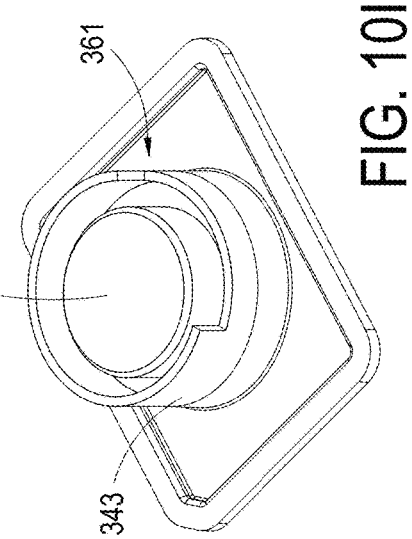

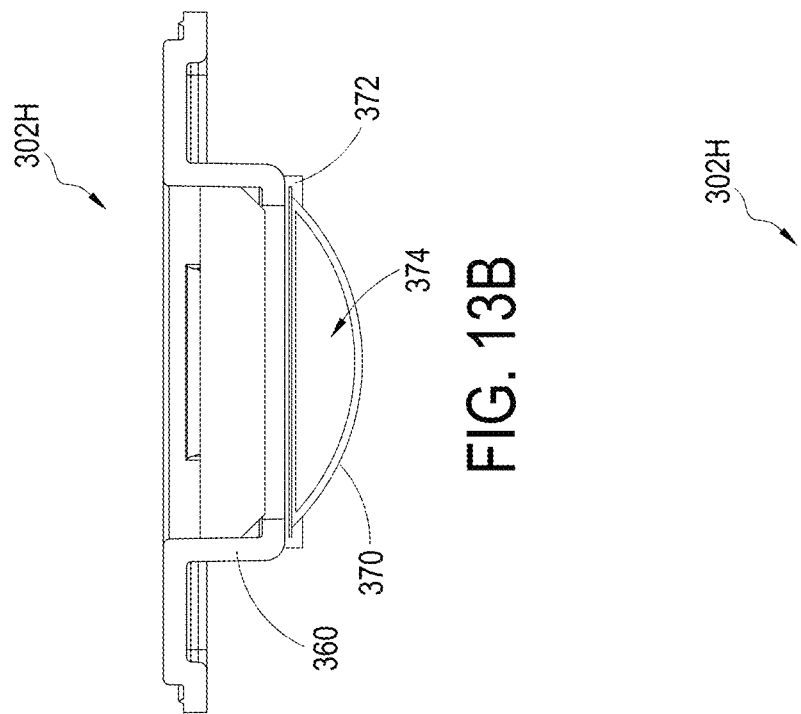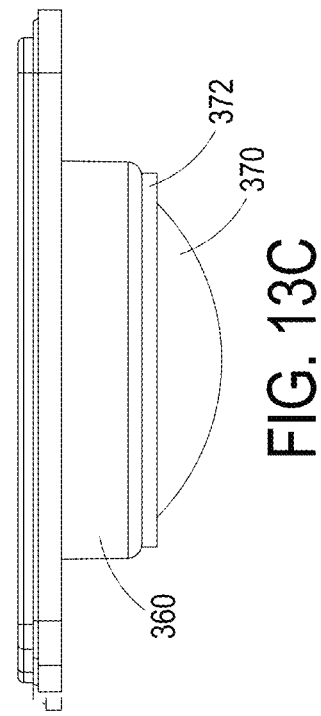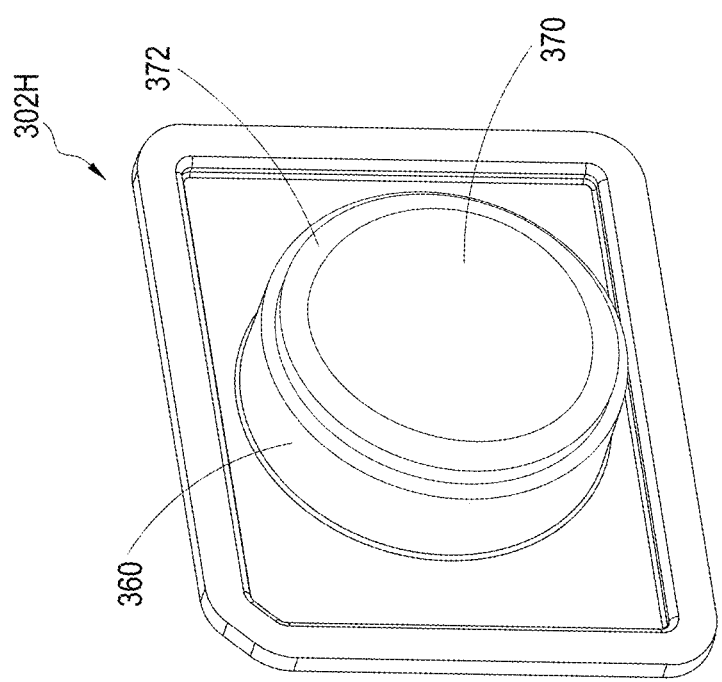

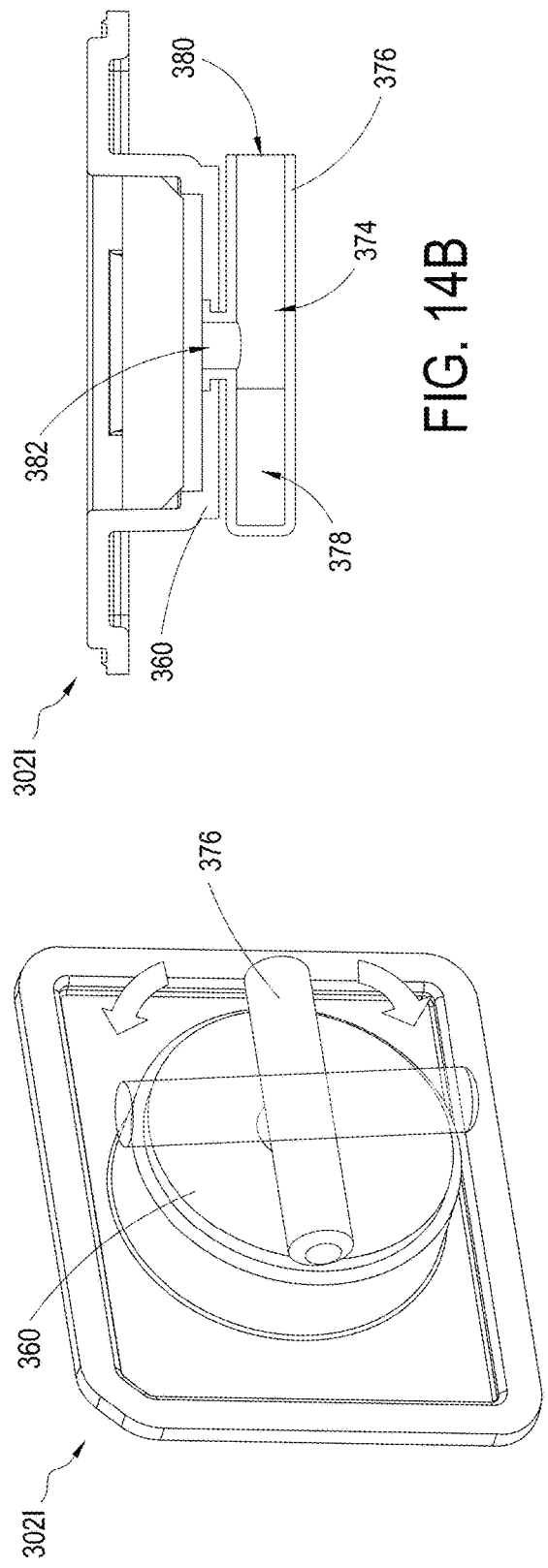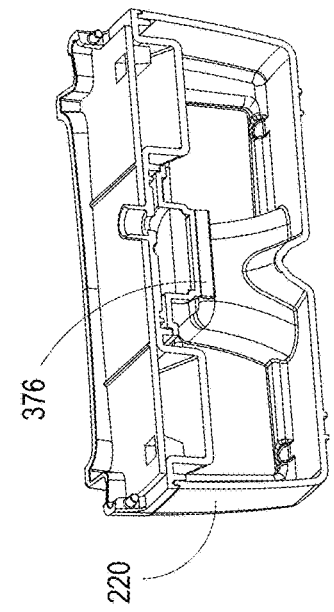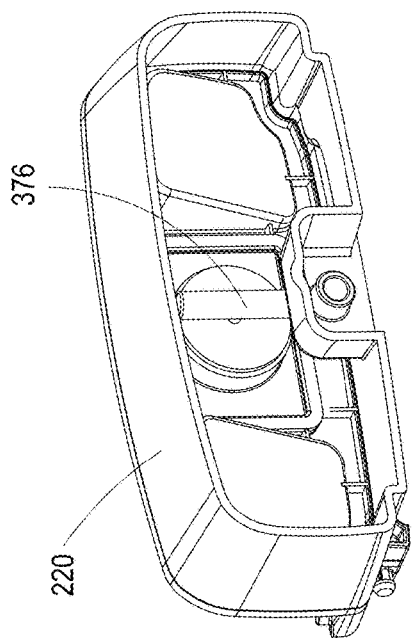

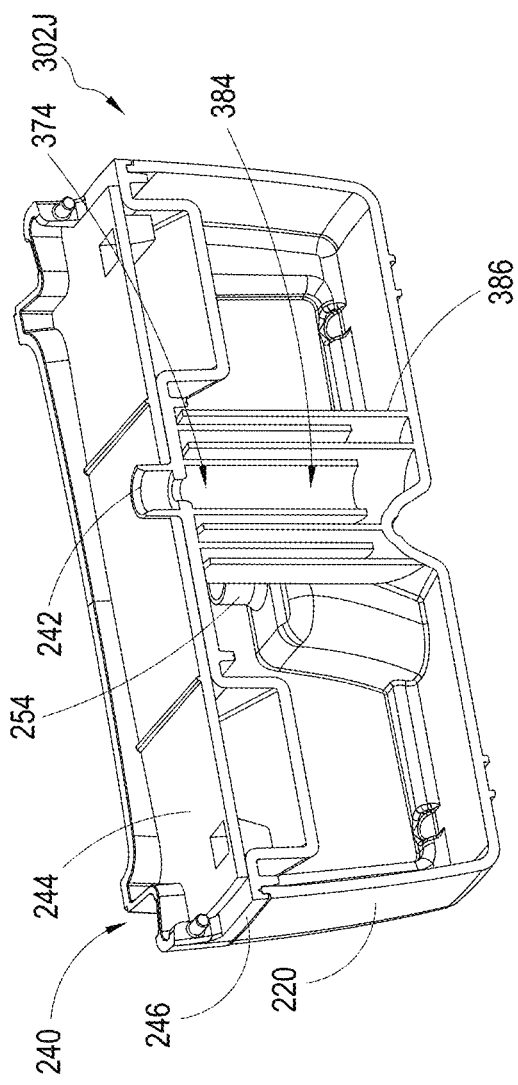
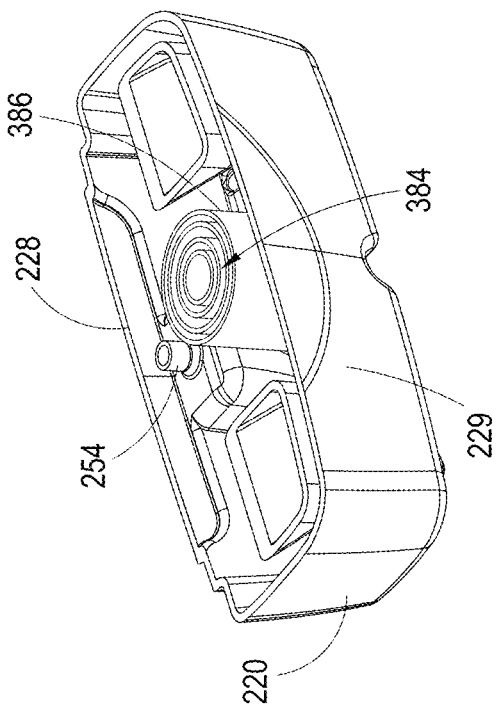
FIG. 15A
FIG. 15B

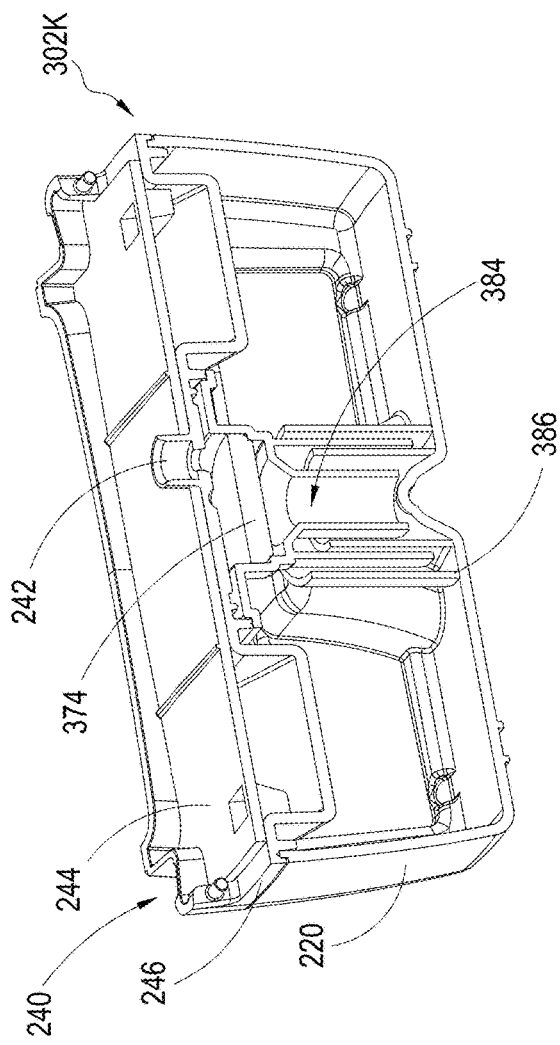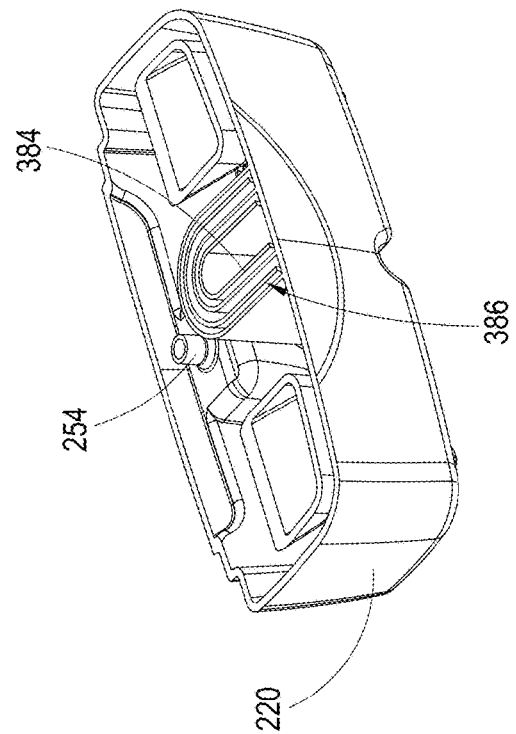

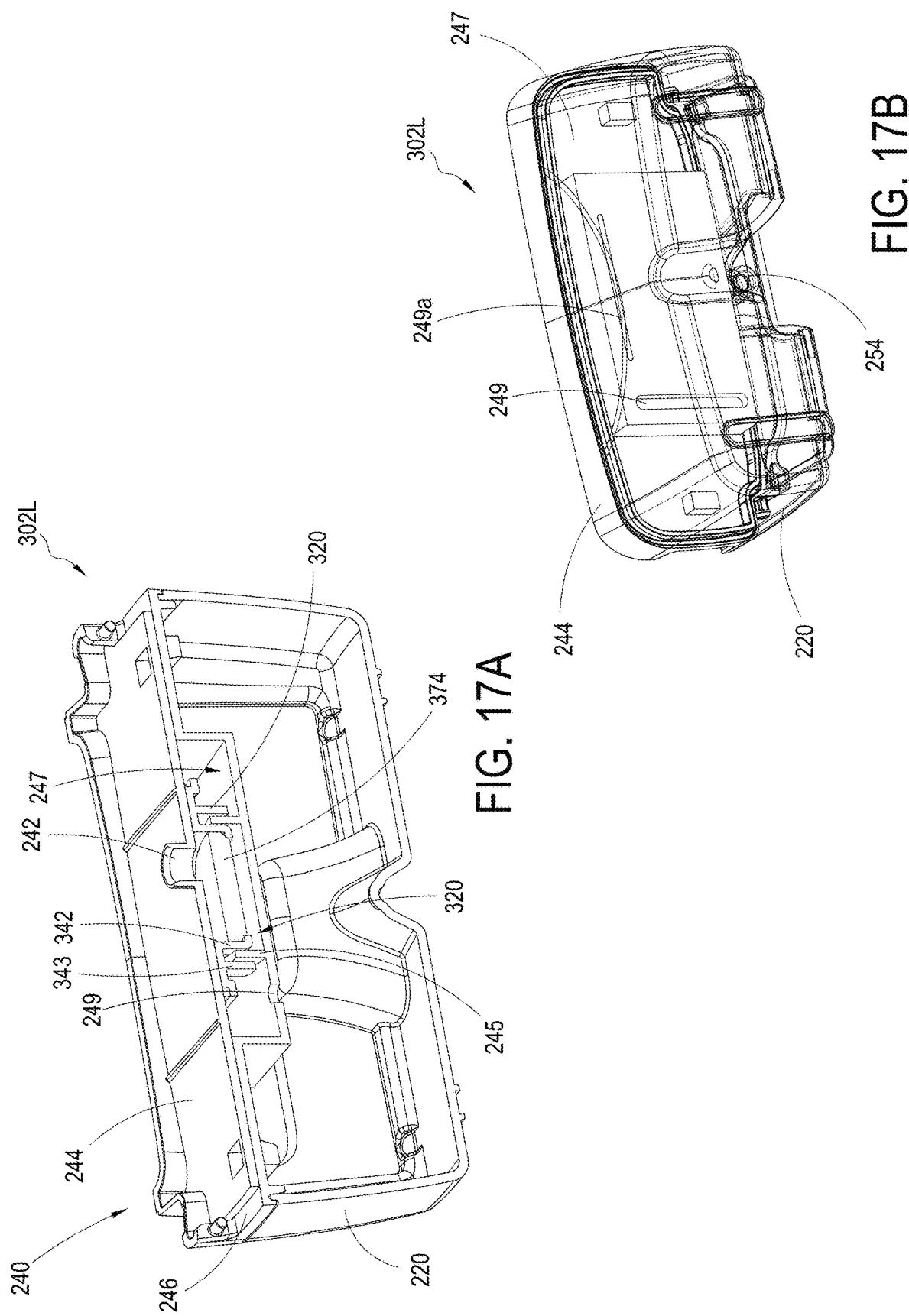

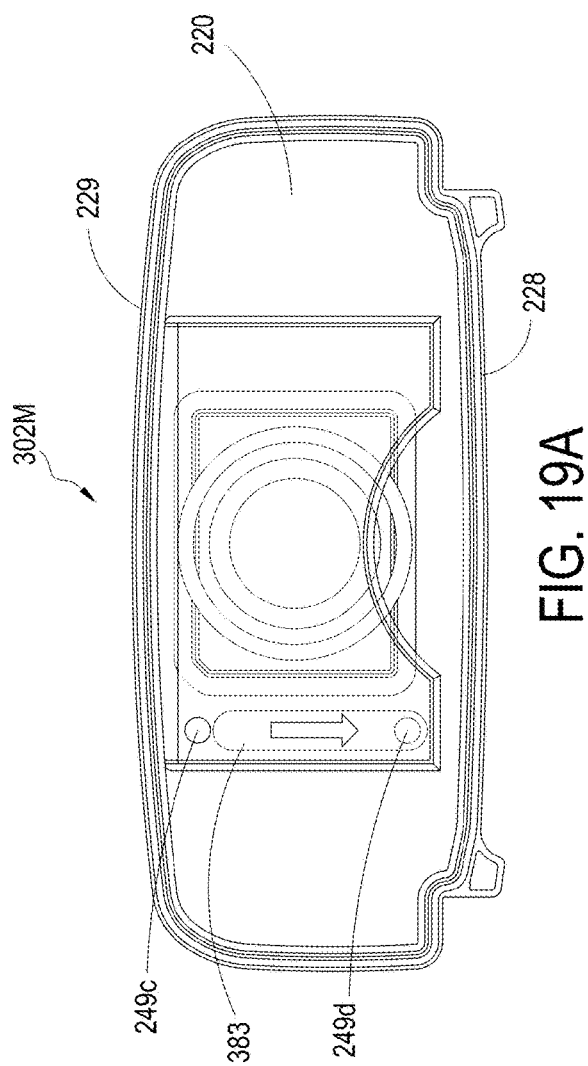
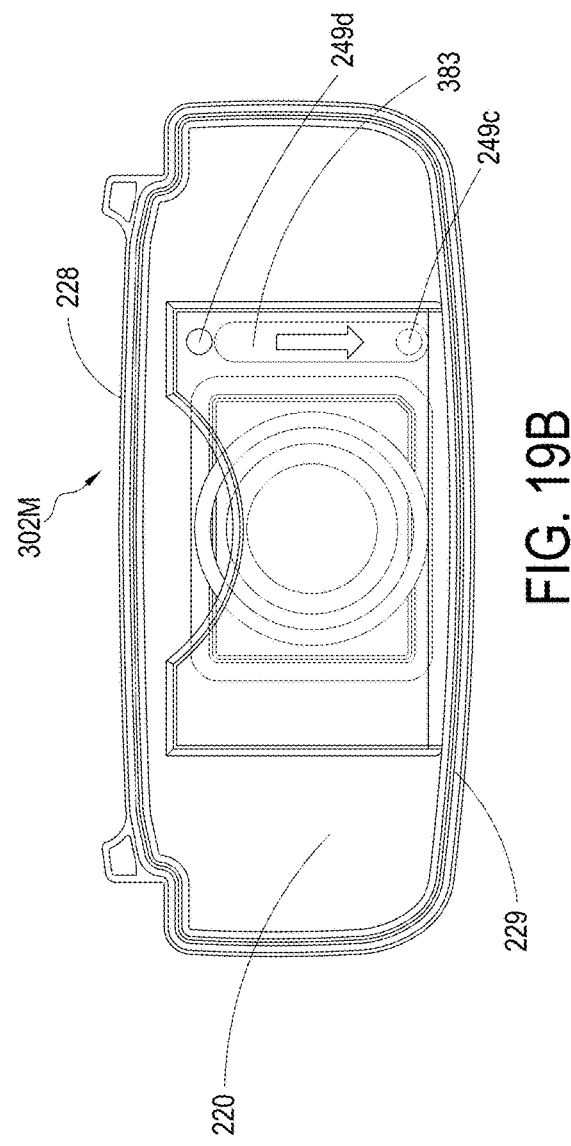

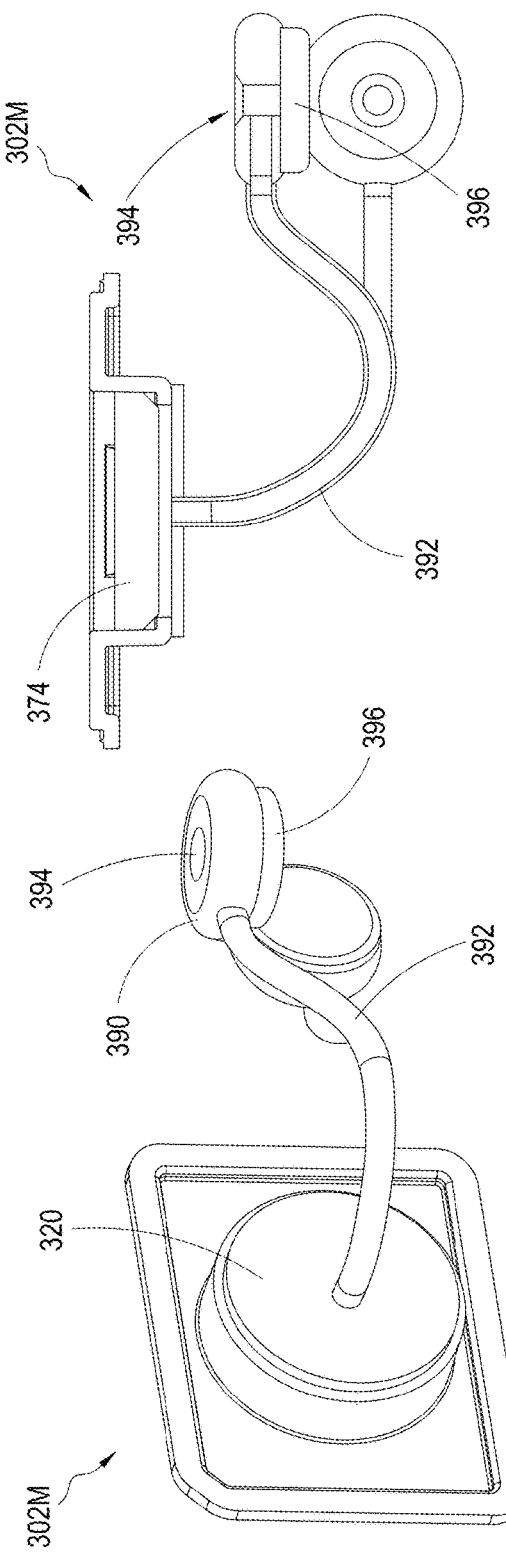
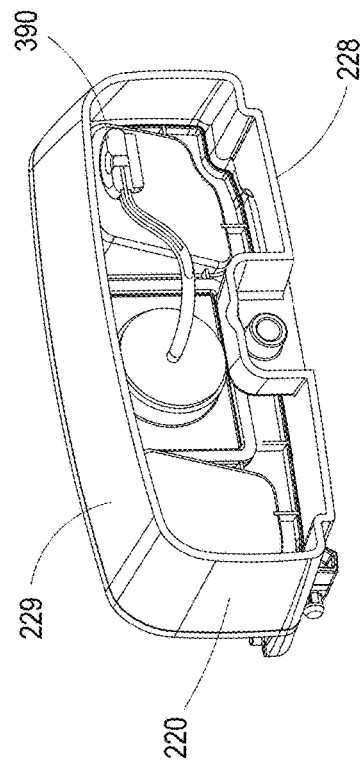
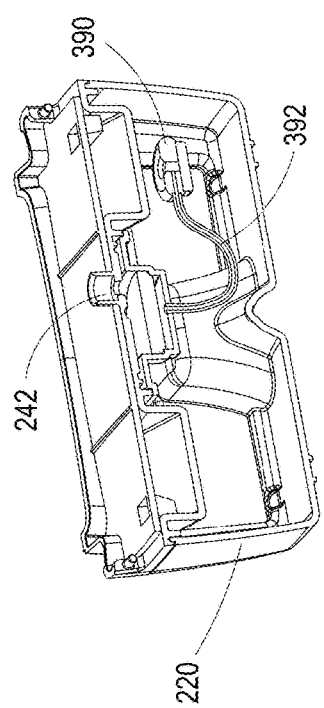
FIG. 20A
FIG. 20B
FIG. 20C
FIG. 20D

NEGATIVE PRESSURE WOUND THERAPY CANISTERS

CROSS-REFERENCE TO RELATED APPLICATIONS

This application is a national stage application under 35 U.S.C. § 371 of International Application No. PCT/US2018/028004, filed on Apr. 17, 2018, which published in English as WO 2018/195101 A1 on Oct. 25, 2018, and which claims priority benefit of U.S. Patent Application No. 62/487,249, filed on Apr. 19, 2017, and U.S. Patent Application No. 62/563,004, filed on Sep. 25, 2017.

BACKGROUND

Embodiments of the present disclosure relate to methods and apparatuses for dressing and treating a wound with reduced pressure therapy or topical negative pressure (MP) therapy. In particular, but without limitation, embodiments disclosed herein relate to negative pressure therapy devices having canisters adapted to receive wound exudate, methods for controlling the operation of TNP systems, and method of using TNP systems.

SUMMARY

Embodiments of the present disclosure relate to apparatuses and methods for wound treatment. Some of the wound treatment apparatuses described herein comprise a pump system or assembly for providing negative pressure to a wound site. Wound treatment apparatuses may also comprise wound dressings that may be used in combination with the pump assemblies described herein, and connectors for connecting the wound dressings to the pump assemblies.

In some embodiments, a canister for a negative pressure wound therapy apparatus is disclosed. The canister includes a receptacle, a connector, and a filter assembly. The receptacle is in fluid communication with a dressing covering a wound and is configured to receive an exudate from the wound. The connector is in fluid communication with a pump assembly. The filter assembly is disposed between the receptacle and the connector and defines a flow path therebetween. The filter assembly has a central portion, a barrier, and a shelf. The central portion extends longitudinally away from a peripheral portion and has a lateral wall and a base. At least a portion of the lateral wall extends circumferentially about the base and connects the base to the peripheral portion. The barrier extends from a connector-side surface of the base. The shelf extends radially inward from the lateral wall. At least a portion of the shelf extends only partially between the lateral wall and the barrier, leaving a gap that provides fluid communication between the connector and the flow path.

The canister of the preceding paragraph can further include one or more of the following features: At least a portion of the shelf radially overlaps with at least a portion of the base. The barrier is substantially perpendicular to the base. The flow path includes an entrance disposed on a radially outward surface of the lateral wall. The entrance is disposed entirely on a radially outward surface of the lateral wall. The entrance has a circumferential extension of about 180 degrees. The filter assembly further includes a filter selected from the group consisting of a hydrophobic filter, a hydrophilic filter, an exclusion filter, an antibacterial filter, and an odor filter.

In some embodiments, a canister for a negative pressure wound therapy apparatus is disclosed. The canister includes a receptacle, a connector, and a filter assembly. The receptacle is in fluid communication with a dressing covering a wound and is configured to receive an exudate from the wound. The connector is in fluid communication with a pump assembly. The filter assembly is disposed between the receptacle and the connector and defines a flow path therebetween. The filter assembly has a central portion and a guard. The central portion includes a longitudinal wall, a shelf, and an inner rim. The inner rim circumferentially surrounds a central opening and is connected to the longitudinal wall by the shelf. The guard is attached to a canister side surface of the shelf and extends radially across the central opening.

The canister of the preceding paragraph can further include one or more of the following features: The guard includes a flange that extends from a pump-side surface of the guard. The flange is disposed radially outward of the inner rim. A notched section of the flange leaves an entrance gap between the flange and the shelf, providing fluid communication between the receptacle and the flow path. The inner rim includes a notched portion that forms an exit gap between the inner rim and the guard and provides fluid communication between the connector and the flow path. The notched section is located circumferentially opposite of the notched portion. The guard further includes one or more hurdles that extend from the pump-side surface of the guard. The hurdles span from the flange to the inner rim. At least one of the one or more hurdles extends only partially between the flange and the shelf. The guard is ultrasonically welded to the shelf. The canister further includes a filter selected from the group consisting of a hydrophobic filter, a hydrophilic filter, an exclusion filter, an antibacterial filter, and an odor filter.

In some embodiments, a canister for a negative pressure wound therapy apparatus is disclosed. The canister includes a receptacle, a connector, and a filter assembly. The receptacle is in fluid communication with a dressing covering a wound and is configured to receive an exudate from the wound. The connector is in fluid communication with a pump assembly. The filter assembly is disposed between the receptacle and the connector and defines a flow path therebetween. The filter assembly has an inner rim, an outer rim, and a shelf connecting the inner rim to the outer rim. The filter assembly further includes a guard, a nesting baffle, and an aperture. The guard is attached to the canister. The nesting baffle extends from a pump-side surface of the guard and is disposed between the inner rim and the outer rim. The aperture is disposed on the pump-side surface of the guard.

The canister of the preceding paragraph can further include one or more of the following features: The aperture is a slot that is substantially perpendicular to a front surface of the canister. The pump-side surface of the guard is sloped to facilitate a liquid on the pump-side surface of the guard draining toward the aperture. The canister further includes a filter selected from the group consisting of a hydrophobic filter, a hydrophilic filter, an exclusion filter, an antibacterial filter, and an odor filter.

BRIEF DESCRIPTION OF THE DRAWINGS

Embodiments of the present disclosure will now be described hereinafter, by way of example only, with reference to the accompanying drawings in which:

FIG. 5 is a exploded view of a filter stack.
FIG. 6A is a cross-sectional view of a filter carrier.
FIG. 6B is a top view of the filter carrier of FIG. 6A.
FIG. 6C is a side cross-sectional view of the filter carrier of FIG. 6A.
FIG. 7C is a side view of a filter carrier.
FIG. 7D is a side cross-sectional view of the filter carrier of FIG. 7C.
FIG. 7F is a side view of a filter carrier.
FIG. 7F is a side cross-sectional view of the filter carrier of FIG. 7E.
FIG. 7G is a pump-side view of an exit of the filter carrier of FIG. 7E.
FIG. 10F is a partial side cross-sectional view of a filter carrier.
FIG. 10G is a pump-side perspective view of the guard of the filter carrier of FIG. 10F.
FIG. 10H is a canister-side perspective view of the base of the filter carrier of FIG. 10F.
FIG. 10I is a canister-side perspective view of the guard of FIG. 10G attached to the base of FIG. 10H.
FIG. 13A is a bottom view of a filter carrier.
FIG. 13B is a side cross-sectional view of the filter carrier of FIG. 13A.
FIG. 13C is a side view of the filter carrier of FIG. 13A.
FIG. 14A is a bottom view of a filter carrier.
FIG. 14B is a side cross-sectional view of the filter carrier of FIG. 14A.
FIG. 14C is a cross-sectional view of a canister on its back.
FIG. 14D is a cross-sectional view of a canister in an upright orientation.
FIG. 15A is a side cross-sectional view of a filter carrier and canister.
FIG. 15B is a top cross-sectional view of the filter carrier and canister of FIG. 15A.
FIG. 16A is a side cross-sectional view of a filter carrier and canister.
FIG. 16B is a top cross-sectional view of the filter carrier and canister of FIG. 16A.
FIG. 17A is a side cross-sectional view of a filter carrier and canister.
FIG. 17B is a bottom view of the filter carrier of FIG. 17A when the canister is oriented on its back.
FIG. 19A is a cross-sectional view of the filter carrier of FIG. 18A when the canister is resting on its back.
FIG. 19B is a cross-sectional view of the filter caner of FIG. 18A when the canister is resting on its front.
FIG. 20A is a bottom view of a filter carrier.
FIG. 20B is a side cross-sectional view of the filter carrier of FIG. 20A.
FIG. 20C is a cross-sectional view of the filter carrier of FIG. 20A when the canister is upright.
FIG. 20D is a cross-sectional view of the filter carrier of FIG. 20A when the canister is resting on its back.

DETAILED DESCRIPTION

Overview

Embodiments disclosed herein relate to systems and methods of treating a wound with reduced pressure. As is used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects absolute pressure that is X mmHg below, for example, 760 mmHg or, in other words, an absolute pressure of (760-X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is farther from atmospheric pressure (e.g., –80 mmHg is more than –60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist hi the healing of surgically closed wounds by removing fluid. In some embodiments TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
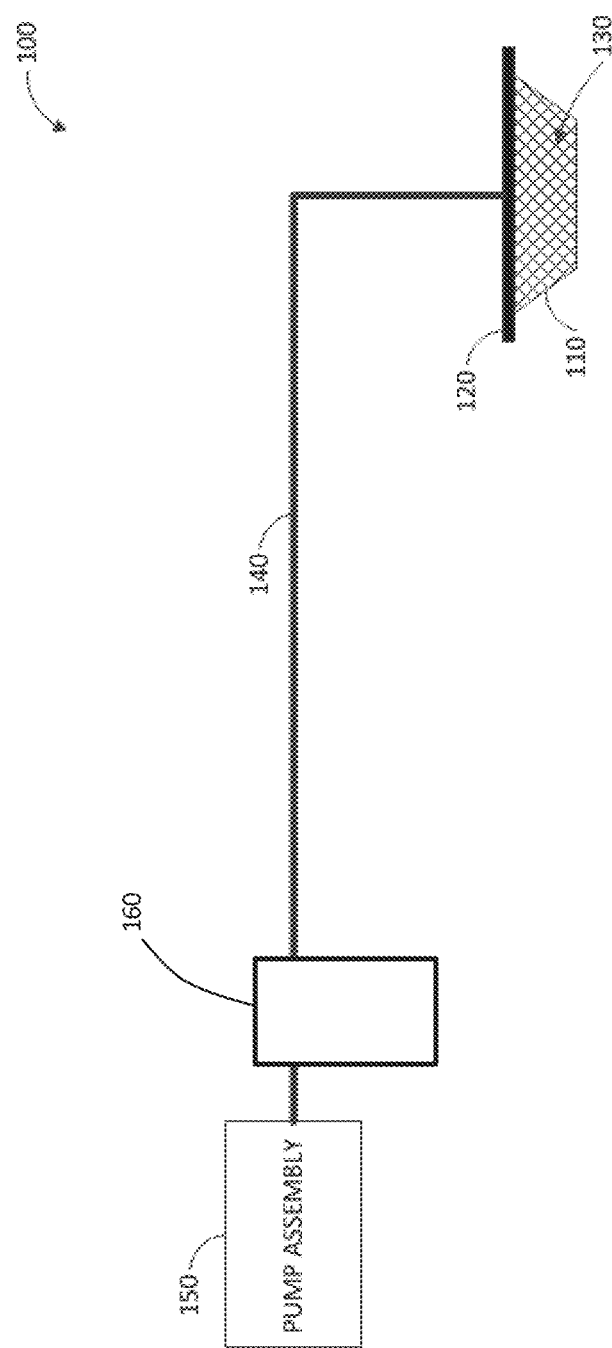
FIG. 1 illustrates a reduced pressure wound therapy system including a pump assembly according to some embodiments.

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi-lumen tube or conduit 140 connects the wound cover 120 with a pump assembly 150 configured to supply reduced pressure. The conduit 140 can be in fluidic communication with the wound cavity 110. In any of the system embodiments disclosed herein, as in the embodiment illustrated in FIG. 1, the pump assembly can be configured to include or support a canister 160. However, any of the pump assembly embodiments disclosed herein can be a canisterless pump assembly (meaning that exudate is collected in the wound dressing or is transferred via tube 140 for collection to another location). At the beginning of the application of negative pressure wound therapy to a wound when the wound is in the early stages of the healing process and exudes a significant volume of exudate, the reduced pressure wound therapy system 100 may operate with a canister 160. In this mode of operation, the negative pressure wound therapy system 100 may operate with a foam or gauze RENASYS™ dressing sold by Smith & Nephew or any other suitable dressing. As the wound is progressing through the healing process and is starting to exude a smaller volume of exudate, the canister 160 may be removed and the negative pressure wound therapy system 100 may operate with an absorbent dressing, such as the PICO™ dressing sold by Smith & Nephew or any other suitable dressing that retains the wound exudate within the dressing. Further details of absorbent dressings such as the PICO™ dressing are found in U.S. Pat. No. 9,061,095, filed on Apr. 21, 2011, and incorporated in its entirety by reference herein. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to the wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the system are designed to operate without the use of an exudate canister 160. Some embodiments can be configured to support an exudate canister 160. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing 140 and the pump 150.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister 160. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith &. Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325 and U.S. patent application Ser. No. 13/287,897, which are assigned to the assignee of present application and are incorporated by reference in their entirety. In other embodiments, other suitable wound dressings can be utilized.

Pump Assembly and Canister

Figure 2A:
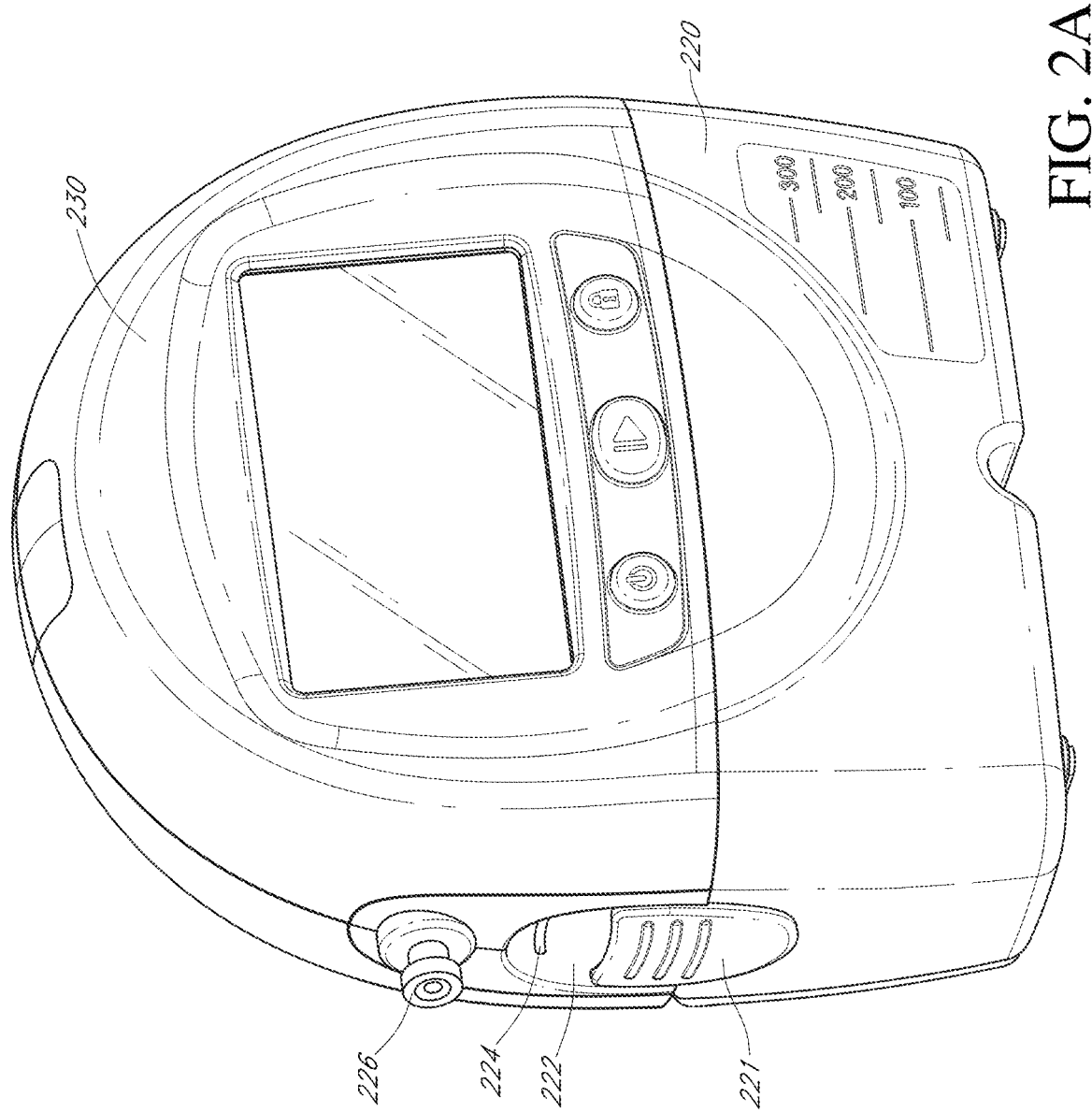
FIG. 2A illustrates a front view of a pump assembly connected to a canister.

FIG. 2A illustrates a front view of a pump assembly 230 and canister 220 according to some embodiments. As is illustrated, the pump assembly 230 and the canister 220 are connected, thereby forming a device. The pump assembly 230 can include one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly 230 can be passed through one or more suitable filters (described below, such as in FIG. 5), such as antibacterial filters. This can maintain reusability of the pump assembly 230. The pump assembly 230 can include one or more strap mounts 226 for connecting a carry strap to the pump assembly 230 or for attaching a cradle. In the illustrated embodiment, two strap mounts 226 can be formed on the sides of the pump assembly 230. Further details of pump assembly are found in U.S. patent application Ser. No. 14/210,062, entitled SYSTEMS AND METHODS FOR APPLYING REDUCED PRESSURE THERAPY, filed on Jul. 3, 2014, and incorporated in its entirety by reference herein.

Figure 2B:
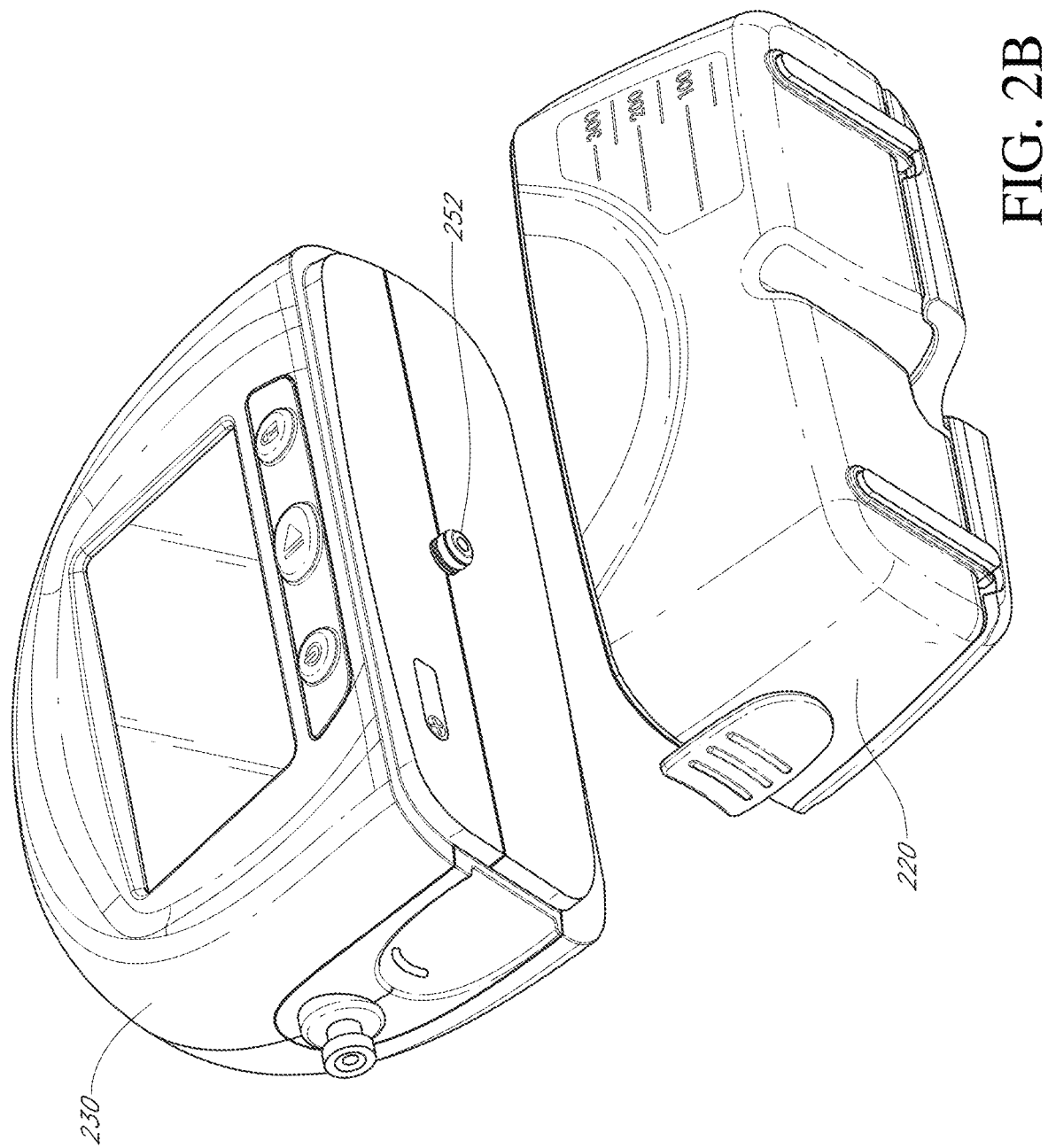
FIG. 2B illustrates an exploded view of the pump assembly and canister of FIG. 2A.

FIG. 2B shows a partial bottom view of the pump assembly 230 separated from the canister 220 according to some embodiments. The pump assembly 230 can include a vacuum attachment or connector 252 through which a vacuum pump communicates negative pressure to the canister 220.

Figure 3:
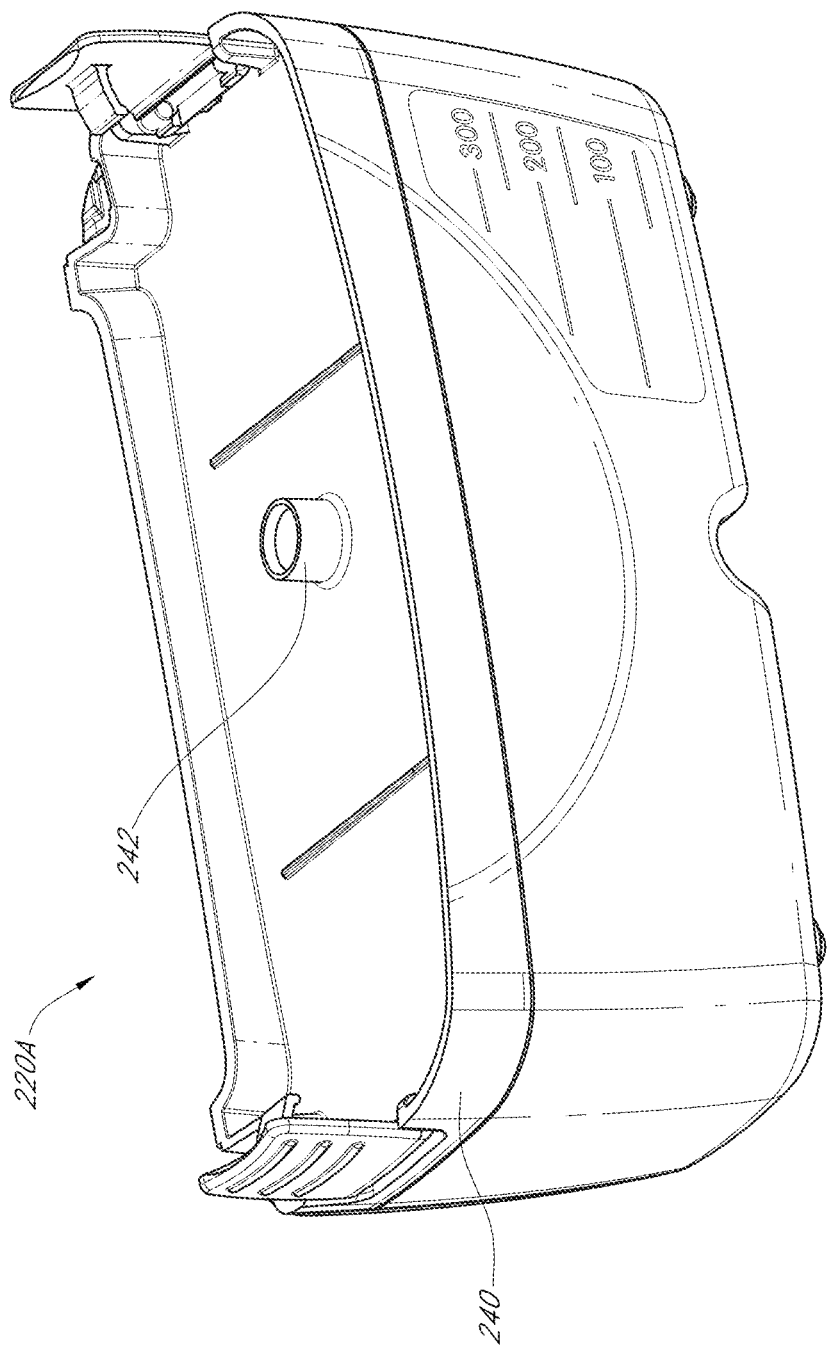
FIG. 3 illustrates a top view of a canister.

FIG. 3 shows a canister 220A similar to the canister 220 except as described differently below. The features of the canister 220A can be combined or included with the canister 220 or any other embodiment discussed herein. In the illustrated embodiment, the canister 220A has a capacity of approximately 300 mL. In some embodiments, the canister 220A can have a capacity other than 300 mL (e.g., 800 mL). The canister 220A can include a bulkhead 240. The bulkhead 240 can include a vacuum attachment or connector 242 through which the canister receives vacuum communicated by the pump assembly 230. In some embodiments, the connector 242 is configured to be connected to or mated with the connector 252 of the pump assembly 230.

Figure 4:
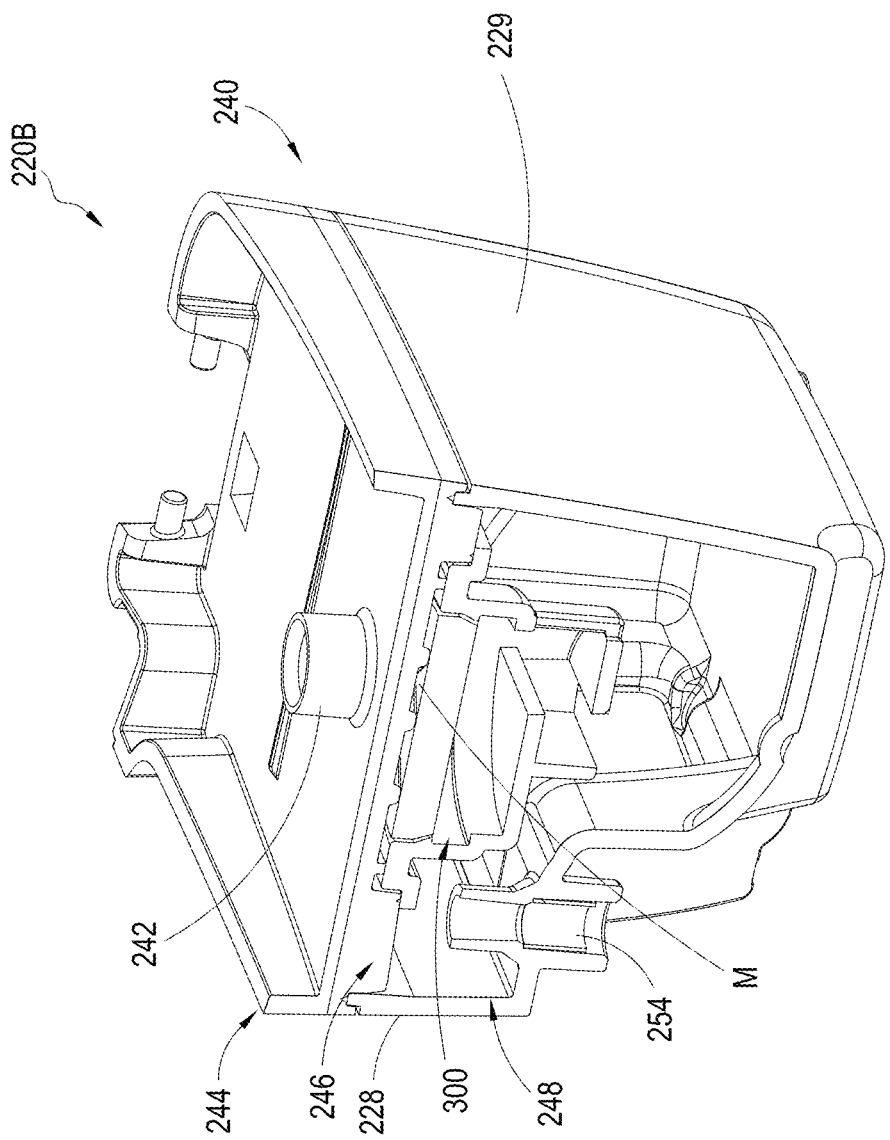
FIG. 4 illustrates a side cross-sectional view of a canister having a filter stack.

FIG. 4 illustrates a cross-sectional side view of a canister 220B similar to the canister 220A except as described differently below. The features of the canister 220B can be combined or included with the canister 220A or any other embodiment discussed herein. In the illustrated embodiment, the bulkhead 240 includes a cap portion 244 and a base portion 246. The canister can include a receptacle 248. The receptacle 248 can be adapted to receive wound exudate that is aspirated from the wound when a negative pressure is applied to the canister 220B through the connector 242 by the pump assembly 230. The bulkhead 240 can be assembled onto the receptacle 248, as shown in FIG. 4. The base portion 246 can be interposed between the receptacle 248 and the cap portion 246 when the bulkhead 240 is assembled onto the receptacle 248. The canister 220B can include a canister filter stack 300. The canister filter stack 300 can be attached to the base portion 246 of the bulkhead 240. As shown in FIG. 4, the canister filter stack 300 can be positioned near an inflow port 254 through which wound exudate can be drawn into the receptacle 248 when a negative pressure is applied to the canister 220B. In the illustrated embodiment, the canister filter stack 300 and the inflow port 254 are both located along a sagittal plane that passes through the back surface 228 and the front surface 229 of the canister 220B. In some arrangements, the canister filter stack 300 and the inflow port 254 can be positioned away from one another. For example, the filter stack 300 can be positioned near a corner formed by the right side and the front surface 229 of the canister 220B while the inflow port 254 is located near a corner formed by the left side and the rear surface 228 of the canister 220B. In some embodiments, the canister stack 300 can be positioned away from the inflow port 254 to avoid frothing at the inflow port 254 from entering the filter stack 300.

FIG. 5 illustrates an embodiment of a canister filter stack 300A similar to the canister filter stack 300 except as described differently below. The features of the canister filter stack 300A can be combined or included with the canister filter stack 300 or any other embodiment discussed herein. The canister filter stack 300A can include a filter carrier 302, a shutoff 304, an odor filter 306, and an antibacterial filter 308. The shutoff 304, the odor filter 306, and the antibacterial filter 308 can be arranged in any order. For example, the odor filter 306 can be disposed between the shutoff 304 and the antibacterial filter 308, as shown in FIG. 5, while in other arrangements the shutoff 304 can be disposed between the odor filter 306 and the antibacterial filter 308. The shutoff 304 can operate to stop suction when the canister 220 becomes full such that canister overfill is prevented. The shutoff 304 can be formed out of hydrophilic material. The odor filter 306 can comprise material that absorbs, reduces or eliminates odor. For example, such material can be active carbon, activated charcoal, or the like. The material can be hydrophobic. In some arrangements, the device can use a catalytic-type converter to oxidize odors. In some variants, the odor filter 306 can include materials that chemically neutralize odors. The odor filter 306 can include anionic, cationic, acid, or basic chemically-modified polymers that chemically react with odors. These materials can work well in the moist or humid conditions that would be present in the wound. The antibacterial filter 308 can inhibit or eliminate the growth of microorganisms. In some embodiments, the components of the filter stack 300 can be arranged in any suitable order. For example, the odor filter 306 can be integrated into the shutoff 304 as an additive to the material of the shutoff 304 or as a layer formed on the material of the shutoff 304. In some embodiments, the filter stack 300 is placed in the canister 220. In some embodiments, the filter stack 300 is placed between the canister 220 and the pump assembly 230. In some embodiments, the filter stack 300 is placed in the pump assembly 230.

With continued reference to FIG. 5, the filter carrier 302 can be adapted to house one or more of the shutoff 304, the odor filter 306, and the antibacterial filter 308. As described in more detail below, the filter carrier 302 can include features that reduce or prevent liquid inside the canister 220 from contacting one or more of the shutoff 304, the odor filter 306, and the antibacterial filter 308. For example, the filter carrier 302 can be arranged to mitigate fluids within the canister 220 from splashing onto the shutoff 304. The filter carrier 302 can be arranged to allow air to traverse from the canister 220 to the pump assembly 230, thereby allowing the pump assembly 230 to create a negative pressure within the canister 220. In some arrangements, the filter carrier 302 includes only one hole for air to traverse to the pump. The filter carrier 302 can be arranged to ensure continual pump operation in one or more likely orientations of the canister 220. The filter carrier 302 can be configured to mitigate issues related to blockages of narrow pathways, as described further below. In some variants, the filter carrier 302 is arranged to mitigate large pressure drops that can significantly increase down times of the pump. As described in more detail below, the filter carrier 302 can be arranged to provide a flow path between the canister and the pump. The flow path can allow the pump assembly 230 to evacuate air from the canister 220, thereby creating a negative pressure within the canister 220 that can draw into the canister 220 wound exudate from the wound dressing. The filter carrier 302 can include features that make the flow path between the canister 220 and the pump 230 more easily navigable by gas (e.g., air) than by liquid (e.g., wound exudate). The filter carrier 302 can include features that prevent wound exudate from passing across the filter carrier 302 and reaching the pump assembly 230 or wetting the filters (e.g., the shutoff 304, the odor filter 306, and the antibacterial filter 308).

FIGS. 6A-6C show a filter carrier 302A similar to the filter carrier 302 except as described differently below. The features of the filter carrier 302A can be combined or included with the filter carrier 302 or any other embodiment discussed herein. The filter carrier 302A can have a central portion 320 that extends from a peripheral portion 322. The filter carrier 302A can be oriented so that the peripheral portion 322 is attached to the bulkhead 240 with the central portion 320 extending toward the canister 220, as shown in FIG. 4. The central portion 320 can include a plurality of upper fins 324 and a plurality of lower fins 326, as shown in FIG. 6A. The upper fins 324 can be disposed between the lower fins 326 and one or more of the shutoff 304, the odor filter 306, and the antibacterial filter 308. The lower fins 326 can be disposed between the upper fins 324 and the wound exudate that has been aspirated into the canister 220, as described above.

In certain arrangements, the upper fins 324 can interdigitate with the lower fins 326, as shown in FIG. 6B. The upper fins 324 and the lower fins 326 can be sized so that a gap 328 is visible between the upper fins 324 and the lower fins 326 when the fins 324, 326 are viewed from the top (e.g., a front view of the surface of the carrier 302A that faces the pump assembly 230). The fins 324, 326 can be arranged so that the gap 328 between the fins forms a single, continuous, serpentine opening (as indicated by the white line in FIG. 6B). The gap 328 can provide a pathway for air to traverse from the interior space of the canister 220 to the connector 242 (shown in FIG. 4), thereby allowing the pump assembly 230 to create a negative pressure inside the canister 220. The fins 324, 326 can create jetty-like structures that prevent wound exudate within the canister 220 from splashing across the fins 324, 326. The fins 324, 326 can be U-shaped. The open portion of the U-shaped upper fins 324 can face the canister 220. The open portion of the U-shaped lower fins 326 can face the pump assembly 230. The U-shaped fins 324, 326 can increase the structural rigidity to the filter carrier 302A. The U-shaped fins 324, 326 can guide liquid back into the canister 220. The fins 324, 326 can allow air to pass by the fins 324, 326, while preventing or inhibiting liquid from passing by the fins 324, 326. The fins 324, 326 can prevent wound exudate within the canister 320 from contacting one or more of the shutoff 304, the odor filter 306, and the antibacterial filter 308.

Figure 7B:
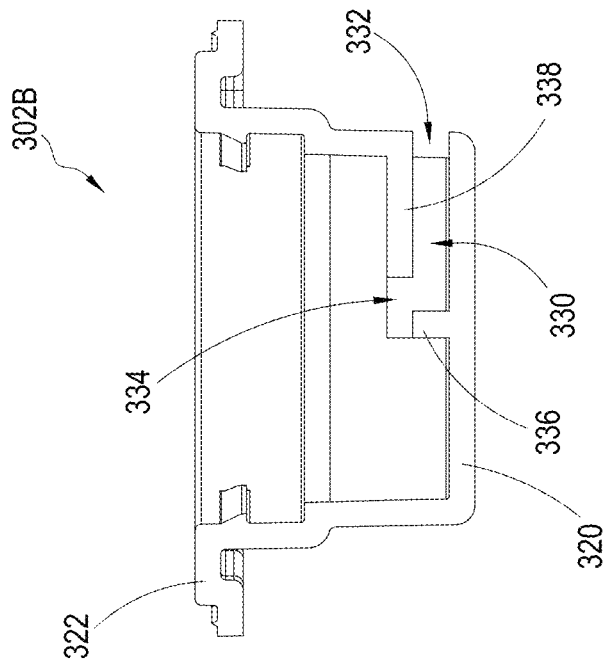
FIG. 7B is a side cross-sectional view of the filter carrier of FIG. 7A.
Figure 7A:
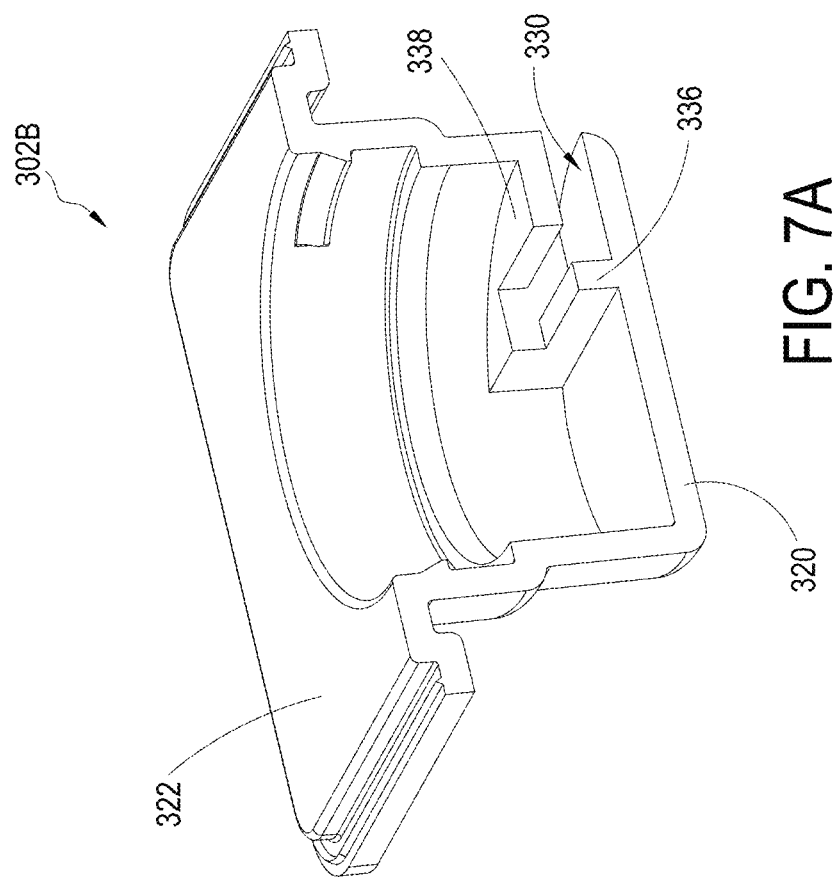
FIG. 7A is a cross-sectional view of a filter carrier.

FIGS. 7A and 7B illustrate a filter carrier 302B similar to the filter carrier 302A except as described differently below. The features of the filter carrier 302B can be combined or included with the filter carrier 302A or any other embodiment discussed herein. The peripheral portion 322 can be disposed closer to the pump assembly 230 than is the central portion 320 when the filter carrier 302B is arranged for use in the TNP system. The central portion 320 of the filter carrier 302B can extend from the peripheral portion 322 into the interior space of the canister 220. The filter carrier 302B can have a passageway 330 that provides a flow path between the connector 242 (shown in FIG. 4) and the receptacle 248 of the canister 220. The passageway 330 can provide a flow path for the pump assembly 230 to draw air out of the canister 220, thereby creating a negative pressure inside the canister 220, as described above. The passageway 330 can have an entrance 332 through which air inside the canister 220 can enter into the passageway 330 when the pump assembly 230 applies a negative pressure to draw air out of the canister 220. The passageway 330 can have an exit 334 through which air can exit the passageway 330 to flow toward the pump assembly 230 when the pump assembly 230 applies a negative pressure to draw air out of the canister 220. As described below, the passageway 330 can be arranged to provide a tortuous path that is easily navigable by gas (e.g., air) but not by liquid (e.g., wound exudate).

Referring to FIG. 7A, the central portion 320 can include a barrier 336. The barrier 336 can extend from the pump-side surface of the central portion 320 in an axial direction toward the pump assembly 230. The barrier 336 can block or inhibit liquid from flowing across the pump-side surface of the central portion 320. The filter carrier 302B can include a top ledge 338 that extends radially inward from an inner surface of the filter carrier 302B toward the barrier 336. A portion of the ledge 338 can join with the barrier 336, as shown in FIG. 7A. A portion of the ledge 338 does not extend to join with the barrier 336, thereby creating a stepped passageway 330 that allows air to flow from the canister 220 toward the pump assembly 230 when the pump assembly 230 applies a negative pressure to draw air out of the canister 220. The stepped passageway 330 is not easily navigable by liquid. Liquid that enters the passageway 330 through the entrance 332 cannot easily flow up the barrier 336 to reach the exit 334. In some embodiments, the passageway 330 can be angled toward the entrance 332 to facilitate draining back into the canister 220 any liquid that enters the passageway 330. As shown in FIG. 7B, the entrance 332 of the passageway 330 can face radially outward, thereby reducing the likelihood that the wound exudate within the canister 220 will enter into the passageway 330. In some arrangements, the entrance 332 can extend circumferentially around a longitudinal axis of the filter carrier 302B that passes through a center of the central portion 320. In certain variants, the entrance 332 has a circumferential extension of about: 45 degree, 90 degrees, 180 degrees, 270 degrees, and values therebetween.

FIGS. 7C and 7D illustrate a filter carrier 302B' similar to the filter carrier 302B except as described differently below. The features of the filter carrier 302B' can be combined or included with the filter carrier 302B or any other embodiment discussed herein. As shown in FIG. 7D, the pump-side surface of the central portion 320 can be substantially co-planar with the pump-side opening of the exit 334. In some embodiments, the pump-side surface of the central portion 320 slopes toward the exit 334 so that any liquid that flows onto the pump-side surface of the central portion 320 will tend to drain back toward the exit 334 to enter the passageway 330. As described above, the pump-side surface of the passageway 330 can be sloped toward the entrance 332 so that liquid in the passageway tends to drain back through the entrance 332 to enter the canister 220.

FIGS. 7E and 7F illustrate a filter carrier 302B" similar to the filter carrier 302B' except as described differently below. The features of the filter carrier 302B" can be combined or included with the filter carrier 302B' or any other embodiment discussed herein. As shown in FIG. 7E, the central portion 320 can extend away from the peripheral portion 322 along a longitudinal axis 10. As discussed above, the filter carrier 302B" can have an entrance 332 that is disposed on an outer longitudinal surface 331 of the filter carrier 302B". In the illustrated embodiment, the entrance 332 circumferentially surrounds the longitudinal axis 10 by more than 180 degrees. In certain variants, the entrance 332 has a circumferential extension of about: 45 degree, 90 degrees, 180 degrees, 270 degrees, and values therebetween.

FIG. 7G shows a pump-side front view of the filter carrier 302B", viewed along the longitudinal axis 10. With reference to FIG. 7G, the entrance 332 extends along the outer longitudinal surface 331 counter-clockwise from point A to point B. In the illustrated embodiment, the entrance 332 has a circumferential extension of about 270 degrees. Referring to FIG. 7F, the ledge 338 can extend from an inner longitudinal surface 333 of the filter carrier 302B". The central portion 320 can include a distal-most central portion 321 and an intermediate central portion 323, with the intermediate central portion 323 being disposed longitudinally between the peripheral portion 322 and the distal-most central portion 321, as shown in FIG. 7F. In the illustrated embodiment, the barrier 336 connects the distal-most central portion 321 to the intermediate central portion 323. In some embodiments, a portion of the ledge 338 extends between the barrier 336 and the exit 334, thereby forming an overhang 335, as shown in FIG. 7F. The overhang 335 can prevent or reduce liquid from splashing through the exit 334 when the liquid contacts the barrier 336. Liquid that enters the entrance 332 and flows along the distal-most central portion 321 may splash upward through the exit 334 when the liquid strikes the barrier 336. The overhang 335 can be sized so that such splashing liquid strikes canister-side surface of the overhang 335, thereby blocking the liquid from passing through the exit 334 and wetting any elements housed within the filter carrier 302B" (e.g., the shutoff 304, the odor filter 306, the antibacterial filter 308).

Figure 7H:
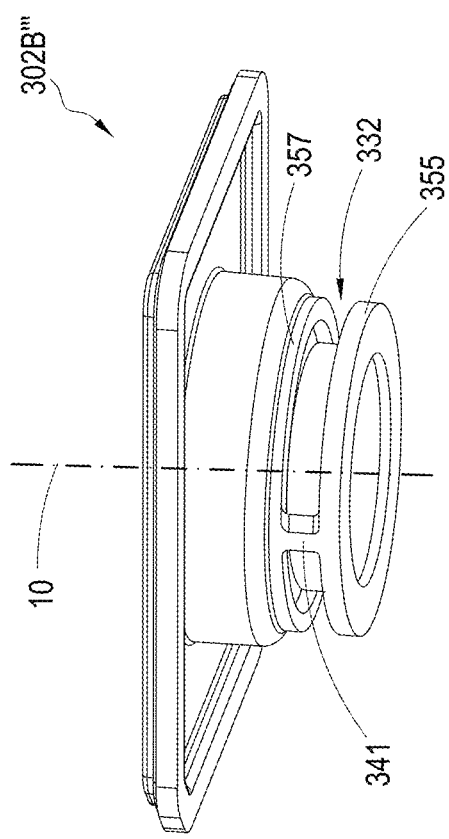
FIG. 7H is a partial bottom view of a filter carrier.
Figure 7I:
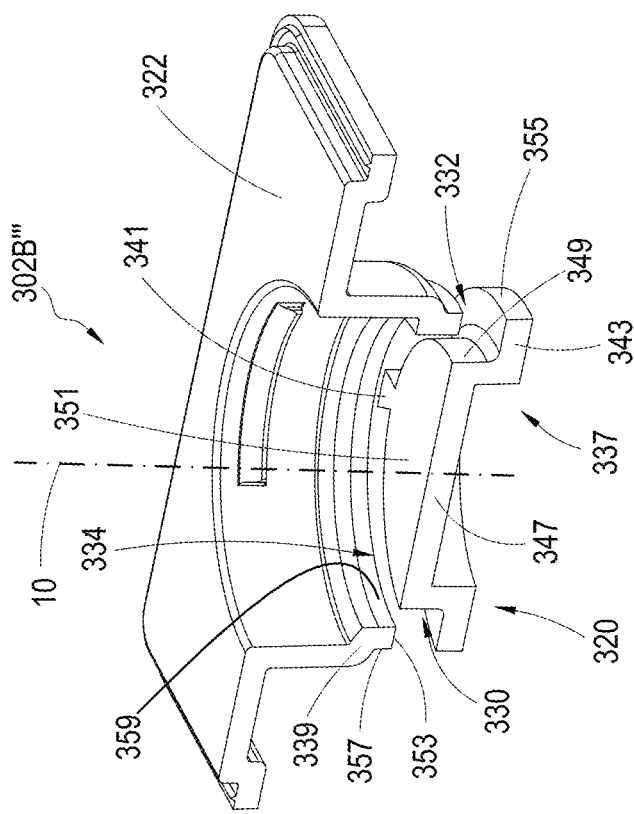
FIG. 7I is a side cross-sectional view of the filter carrier of FIG. 7H.

FIGS. 7H and 7I illustrate a filter carrier 302B''' similar to the filter carrier 302B" except as described differently below. The features of the filter carrier 302B''' can be combined or included with the filter carrier 302B" or any other embodiment discussed herein. As described below, the entrance 332 nearly entirely circumferentially surrounds the longitudinal axis 10. The central portion 320 includes a plug portion 337 and a dock portion 339. A strut 341 connects the plug portion 337 to the dock portion 339, as shown in FIG. 7I. In the illustrated embodiment, the plug portion 337 is connected to the dock portion 339 by only one strut 341. Therefore, the entrance 332 extends circumferentially around the entire periphery of the central portion 320 except for the portion of the periphery that is occupied by the strut 341. In certain variants, the plug portion 337 is connected to the dock portion 339 by more than one circumferentially-spaced-apart strut 341. The number of struts 341 that connect the plug portion 337 to the dock portion 339 can be one, two, three, or more than three.

The flow path 330 of the filter carrier 302B''' is formed by the gap between the plug portion 337 and the dock portion 339. The flow path 330 is configured to be more easily navigable by gas (e.g., air) than by liquid (e.g., wound exudate). Referring to FIG. 7I, the plug portion 337 can have a brim 343 that is disposed radially outward of a crown 347. The crown 347 can extend longitudinally from the brim 343 along the longitudinal axis 10 in the pump-side direction, as shown in FIG. 7I. The crown 347 can have a crown face 351, which is the pump-side surface of the crown 347, as indicated in FIG. 7I. The crown 347 has a crown outer sidewall 349 that circumferentially surrounds the outer periphery of the crown face 351. In the illustrated embodiment, the crown outer sidewall 349 faces the entrance 332. The dock portion 339 can have a dock face 353, which is the canister-side surface of the dock portion 339, as shown in FIG. 7I. In the illustrated embodiment, the crown face 351 is substantially longitudinally aligned with the dock face 353. In other words, the pump-side aspect of the crown 347 extends up to, but not past, the canister-side aspect of the dock portion 339. In some arrangements, the dock face 353 is longitudinally disposed between the crown face 351 and the brim 343 of the plug portion 337. In other words, in some arrangements, the pump-side aspect of the plug portion 337 extends into the dock portion 339. In certain variants, the crown face 351 is longitudinally disposed between the dock face 353 of the dock portion 339 and the brim 343 of the plug portion 337. In other words, the stint 341 connecting the plug portion 337 to the dock portion 339 longitudinally spans a gap formed between the pump-side-most aspect of the plug portion 337 and the canister-side-most aspect of the dock portion 339.

As shown in FIGS. 7H and 7I, the brim 343 can have a brim outer sidewall 355, and the dock portion 339 can have a dock outer sidewall 357. In the illustrated embodiment, the brim outer sidewall 355 has an outer diameter that is substantially equal to that of the dock outer sidewall 357. In some arrangements, the brim outer sidewall 355 has an outer diameter that is larger than that of the dock outer sidewall 357. In some arrangements, the brim outer sidewall 355 has an outer diameter that is smaller than that of the dock outer sidewall 357.

Referring to FIG. 7I, the dock portion 339 can have a dock inner sidewall 359. The dock face 353 extends between the dock inner sidewall 359 and the dock outer sidewall 357. As shown in FIG. 7I, the dock face 353 can radially overlap with the brim 343, forming a portion of the flow path 330 that runs substantially perpendicular to the longitudinal axis 10. In the illustrated embodiment, the radial extent of the dock face 353 is substantially coextensive with the radial extent of the brim 343. In certain arrangements, the brim 343 extends radially beyond the dock face 353. In some embodiments, the dock face 353 extends radially beyond the brim 343, as described previously above.

Figure 8B:
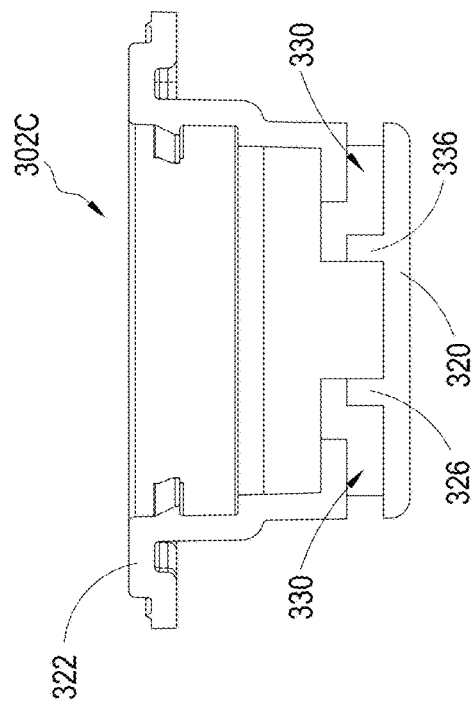
FIG. 8B is a side cross-sectional view of the filter carrier of FIG. 8A.
Figure 8A:
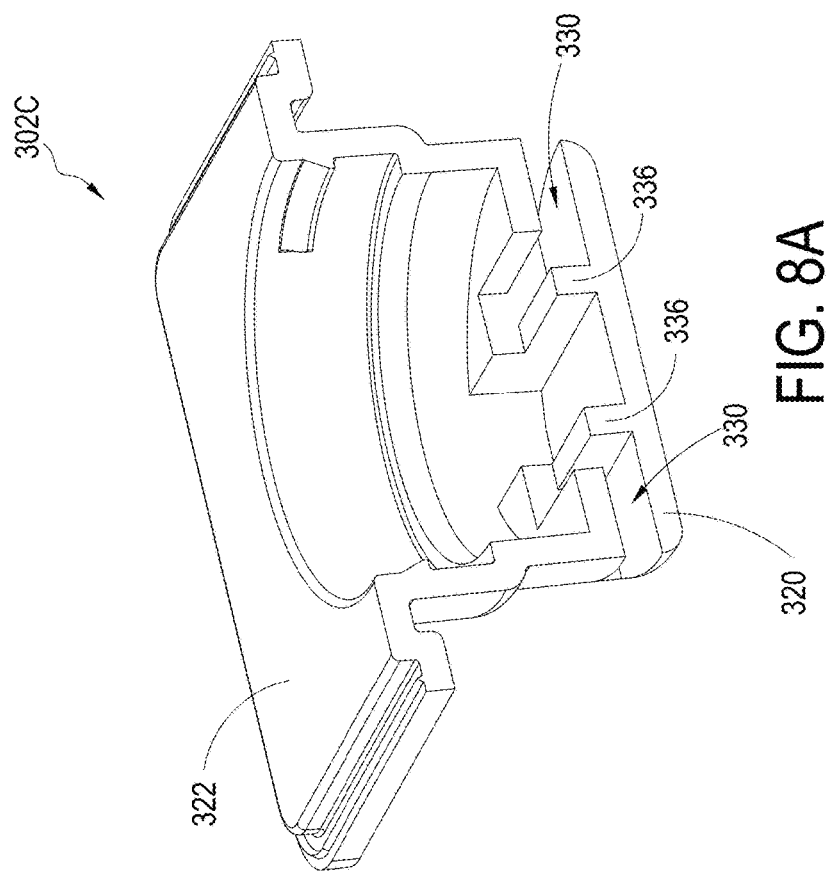
FIG. 8A is a cross-sectional view of a filter carrier.

FIGS. 8A and 8B illustrate a filter carrier 302C similar to the filter carrier 302B except as described differently below. The features of the filter carrier 302C can be combined or included with the filter carrier 302B or any other embodiment discussed herein. The filter carrier 302C can have two spaced-apart walls 336 that extend from the pump-side surface of the central portion 320 in an axial direction toward the pump assembly 230. The filter carrier 302C can have two opposing stepped passageways 330 that extend radially inward to the walls 336, where the passageways 330 and walls or barriers 336 function as described above with regard to the filter carrier 302B shown in FIG. 7A.

Figure 9:
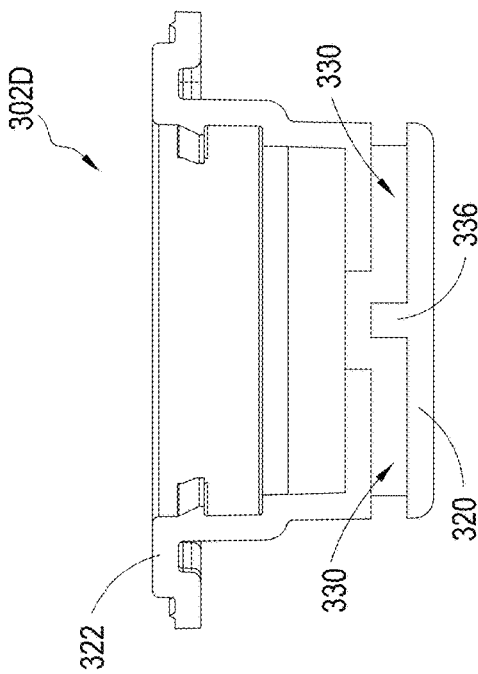
FIG. 9 is a cross-sectional view of a filter carrier.

FIG. 9 shows a filter carrier 302D similar to the filter carrier 302C except as described differently below. The features of the filter carrier 302D can be combined or included with the filter carder 302C or any other embodiment discussed herein. The filter carrier 302D can have two opposing stepped passageways 330 that extend radially inward to a single wall or harrier 336, where the passageways 330 and wall or barrier 336 function as described above with regard to the filter carrier 302C.

FIGS. 10A-10E illustrate a filter carrier 302E similar to the filter carrier 302D except as described differently below. The features of the filter carrier 302E can be combined or included with the filter carrier 302D or any other embodiment discussed herein. As described in more detail below, the filter carrier 302E can include features that form a labyrinth of concentric rings, thereby creating a flow path that is more easily navigable by gas air) than by liquid (e.g., wound exudate).

Figure 10C:
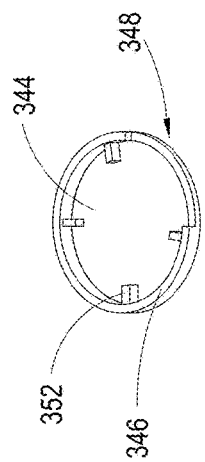
FIG. 10C is a top view of the guard of the filter carrier of FIG. 10A.
Figure 10D:
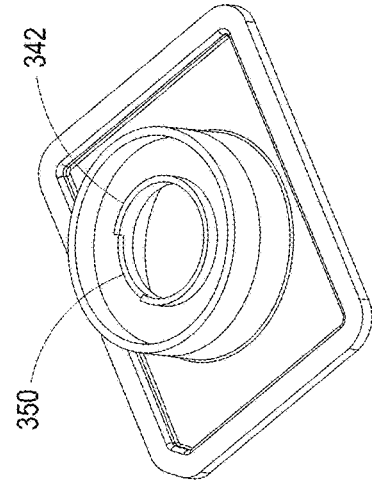
FIG. 10D is a bottom view of the base of the filter carrier of FIG. 10A.
Figure 10E:
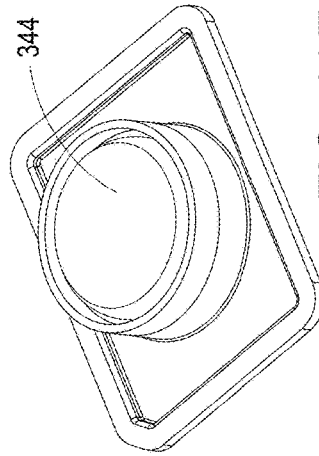
FIG. 10E is a bottom view of the guard of FIG. 10C attached to the base of FIG. 10D.
Figure 10A:
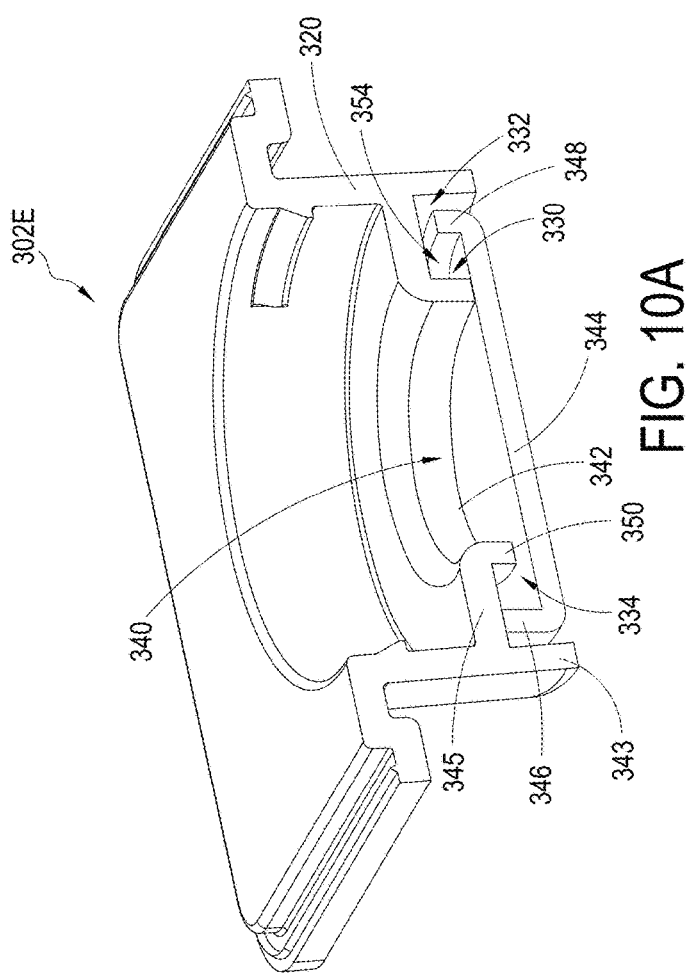
FIG. 10A is a cross-sectional view of a filter carrier.
Figure 10B:
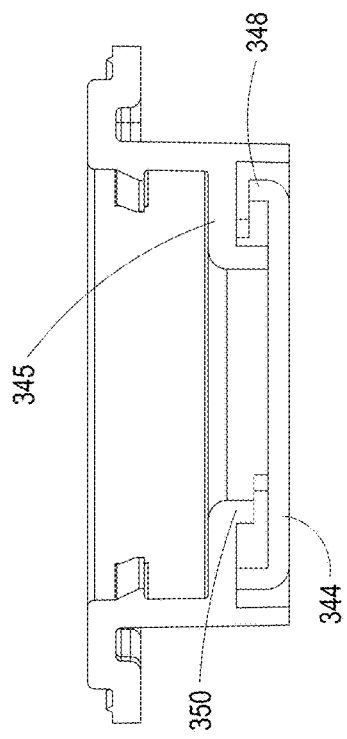
FIG. 10B is a side cross-sectional view of the filter carrier of FIG. 10A.

The filter carrier 302E can include a central opening 340 that is circumferentially surrounded by an inner rim 342, as shown in FIG. 10A. An outer rim 343 can circumferentially surround the inner rim 342. A shelf 345 can connect the outer rim 343 to the inner rim 342, as shown in FIG. 10A. The filter carrier 302E can include a guard 344 that is positioned substantially perpendicular to a longitudinal axis of the central opening 340. The guard 344 can be disposed between the central opening 340 and the interior space of the canister 220 along the longitudinal axis of the central opening 340, as shown in FIG. 10A. The guard 344 can have a flange 346 that circumferentially surrounds the inner rim 342, as shown in FIG. 10A. A section 348 of the flange 346 can have a reduced height compared to adjacent portions of the flange 346, as indicated in FIGS. 10B and 10C. The flange 346 can be attached to the shelf 345 (e.g., by an adhesive). In some embodiments, the flange 346 is ultrasonically welded to the shelf 345. The inner rim 342 can have an area of reduced height that forms a notch 350, as shown in FIG. 10D. The guard 344 can be attached to the shelf 345 so that the section 348 is disposed circumferentially across from the notch 350, as indicated in FIG. 10B.

As shown in FIG. 10C, the guard 344 can include one or more hurdles or protrusions 352 that extend radially inward from the flange 346. As described in more detail below, the hurdles 352 can serve as a barrier that impedes liquid flow along the pump-side surface of the guard 344 when the guard 344 is attached as shown in FIG. 10A to the shelf 345. The hurdles or protrusions 352 can span the gap between the flange 346 and the inner rim 342 when the guard 344 is attached to the shelf 345. One or more of the hurdles 352 can have a height that is smaller than the height of the flange 346, creating a gap between the hurdle 352 and the shelf 345. Air can cross the hurdle 352 by flowing over the hurdle 352 through the gap between the hurdle 352 and the shelf 345. Liquid (e.g., wound exudate) cannot cross the hurdle 352 as easily as air because gravity forces, which are substantially parallel with the height of the hurdle 352, resist liquid flowing over the hurdle 352.

Referring to FIG. 10A, the earner 302E provides a flow path 330 between the central opening 340 and the interior space of the canister 220, The entrance 332 of the flow path 330 is the gap between the section 348 and the shelf 345. The exit 334 of the flow path 330 is the gap between the notch 350 and the guard 344. The entrance 332 is connected to the exit 334 by a channel 354 that is bounded laterally by the inner rim 342 and the flange 348 and bounded axially by the shelf 345 and the guard 344, as shown in FIG. 10A. As discussed, the channel 354 can include one or more hurdles 352 that span between the inner rim 342 and the flange 346. The hurdles 352 may extend only partially across the space between the guard 344 and the shelf 345, leaving a gap that is more easily navigable by gas (e.g., air) than by liquid (e.g., wound exudate), as described previously.

FIGS. 10F-10I illustrate a filter carrier 302E' similar to the filter carrier 302E except as described differently below. The features of the filter carrier 302E' can be combined or included with the filter carrier 302E or any other embodiment discussed herein. The height of the inner rim 342 and the flange 346 can be elongated along the longitudinal axis of the central opening 340 to form deep cavities in the flow path 330 between the guard 344 and the shelf 345, as shown in FIG. 10F. The deep cavities can allow for better airflow through the flow path 330.

The filter carrier 302E' can form a two-part labyrinth of concentric rings, as described below. The outer rim 343 can have a height defined by the extent to which the outer rim 343 extends longitudinally away from the peripheral portion 322. As shown in FIG. 10H, the height of the outer rim 343 can be reduced in a region to form a pass 361. As discussed above, a section 348 of the flange 346 can have a reduced height compared to adjacent portions of the flange 346, as shown in FIG. 10G. The filter carrier 302B' can be arranged so that the pass 361 is circumferentially spaced apart from the section 348 by about 180 degrees, as shown in FIG. 10F.

With continued reference to FIG. 10F, the canister-most surface of the guard 344 can be longitudinally disposed between the canister-most surface of the pass 361 and the canister-most surface of the remaining portion of the outer rim 343. By circumferentially aligning the section 348 with the remaining portion of the outer rim 343, the remaining portion of the outer rim 343 can protect against liquid (e.g., wound exudate) from splashing past the section 348. The filter carrier 302E' is adapted to allow gas (e.g., air) to flow past the guard 344 to access the central opening 340, while inhibiting or preventing liquid (e.g., wound exudate) from flowing past the guard 344 to reach the central opening 340.

As shown in FIG. 10G, the guard 344 can include a pair of spaced apart walls that form an inner corral 363 therebetween. The inner rim 342 can seat into the inner corral 363 when the filter carrier 302E' is assembled, as shown in FIG. 10F. Referring to FIG. 10H, the canister-side surface of the shelf 345 can include a pair of spaced apart walls that form an outer corral 365 therebetween. As shown in FIG. 10F, the flange 346 can seat into the outer corral 365 when the filter carrier 302E' is assembled. The guard 344 can be secured to the shelf 345 and/or to the inner rim 342 by adhesive, ultrasonic welding, or other means known in the art. As shown if FIG. 10F, the guard 344 can include one or more hurdles 352 that impede or block the flow of liquid toward the central opening 340, as discussed above with regard to filter carrier 302E.

FIG. 10I shows a bottom view of the filter carrier 302E'. The pass 361 is visible in FIG. 10I, while the section 348 is hidden from view by virtue of being circumferentially spaced apart from the pass 361 by about 180 degrees. In the illustrated embodiment, the section 348 faces away from the pass 362 and toward the remaining portion of the outer rim 343.

Figure 11B:
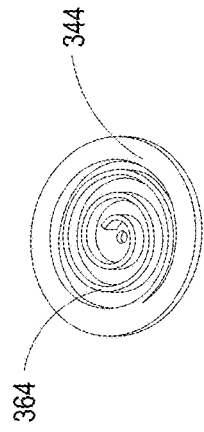
FIG. 11B is a side cross-sectional view of the filter carrier of FIG. 11A.
Figure 11C:
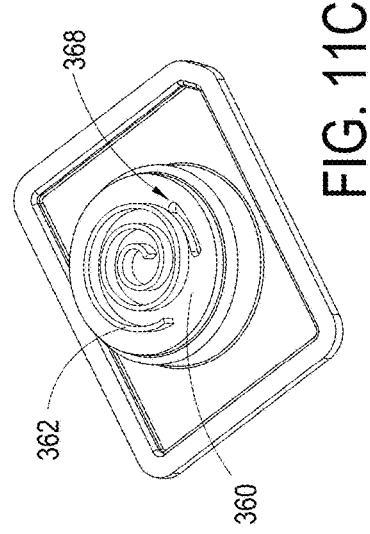
FIG. 11C is a top view of the guard of the filter carder of FIG. 11A.
Figure 11D:
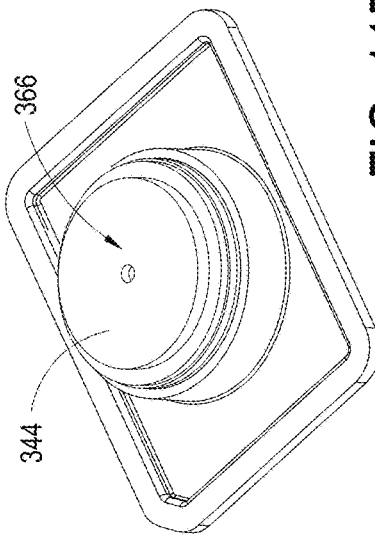
FIG. 11D is a bottom view of the base of the filter carrier of FIG. 11A.
Figure 11A:
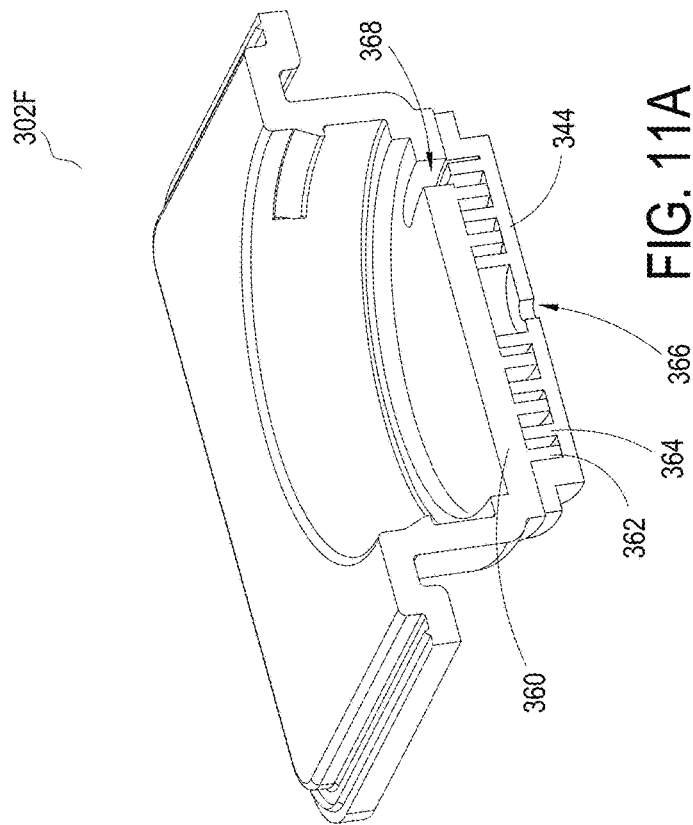
FIG. 11A is a cross-sectional view of a filter carrier.

FIGS. 11A-11D illustrate a filter carrier 302F similar to the filter carrier 302E except as described differently below. The features of the filter carrier 302F can be combined or included with the filter carrier 302E or any other embodiment discussed herein. The filter carrier 302F can have a base 360 that is attached to a guard 344. A spiral-shaped harrier 362 can extend from the base 360. The guard 344 can have a corresponding spiral-shaped harrier 364 that interlaces with the spiral-shaped barrier 362 when the guard 344 is attached to the base 360, as shown in FIG. 11A. The interlaced spiral-shaped walls 362, 364 can define a flow channel therebetween that communicates between a hole 366, for example at or near the center of the guard 344, and a slot 368 in the base 360. Gas (e.g., air) inside the canister 220 can enter the flow channel through the hole 366 and exit the flow channel through the slot 368 to flow toward the pump assembly 230 when the pump assembly 230 applies a negative pressure to the canister 220, as described previously. Liquid (e.g., wound exudate) cannot easily enter the flow channel through the hole 366 and cannot easily navigate the tortuous spiral-shaped flow channel.

Figure 12A:
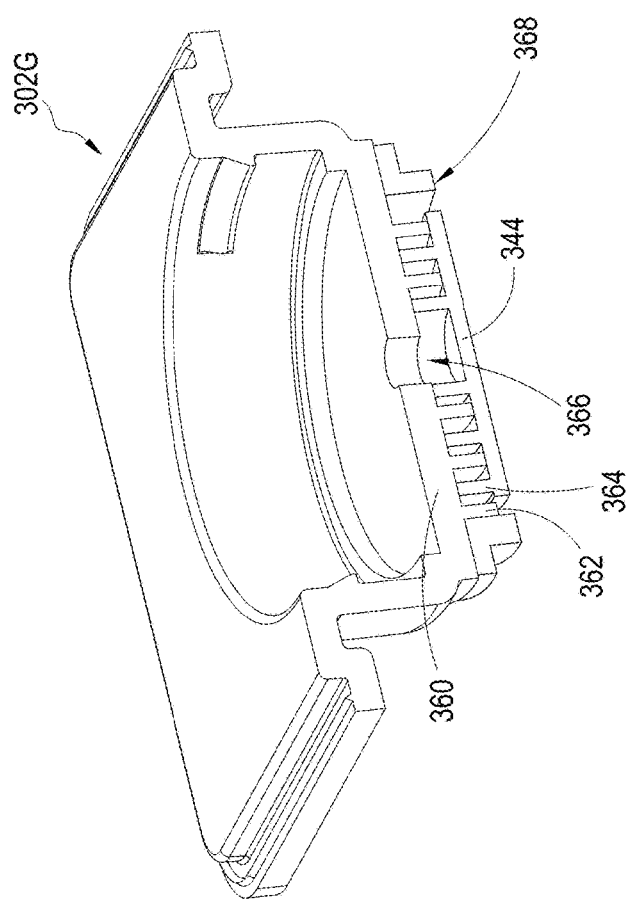
FIG. 12A is a cross-sectional view of a filter carrier.
Figure 12B:
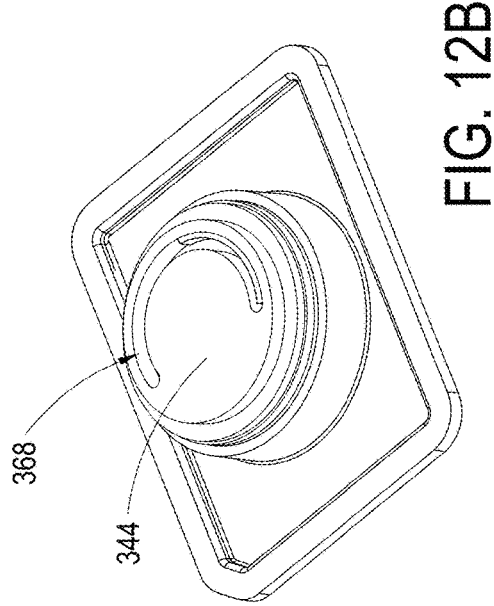
FIG. 12B is a bottom view of the filter carrier of FIG. 12A.

FIGS. 12A and 12B illustrate a filter carrier 302G similar to the filter carrier 302F except as described differently below. The features of the filter earner 302G can be combined or included with the filter carrier 302F or any other embodiment discussed herein. The filter carrier 302G can have a base 360 that is attached to a guard 344. The base 360 can have a spiral-shaped barrier 362 that interlaces with a corresponding spiral-shaped barrier 364 of the guard 344 when the guard 344 is attached to the base 360, as shown in FIG. 12A. The interlaced spiral-shaped walls 362, 364 can form a flow channel therebetween that communicates between a hole 366, for example at or near the center of the base 360, and a slot 368 in the guard 344. Gas (e.g., air) inside the canister 220 can enter the flow channel through the slot 368 and exit the flow channel through the hole 366 to flow toward the pump assembly 230 when the pump assembly 230 applies a negative pressure to the canister 220, as described previously. Liquid (e.g., wound exudate) cannot easily enter the flow channel through the slot 368 and cannot easily navigate the tortuous spiral-shaped flow channel.

FIGS. 13A-13C illustrate a filter carrier 302H similar to the filter carrier 302G except as described differently below. The features of the filter carrier 302H can be combined or included with the filter carrier 302G or any other embodiment discussed herein. The filter carrier 302H can have a mesh 370 that is attached to the base 360 by a collar 372. The mesh 370 can be a tight woven metal mesh. The mesh 370 can have a porosity that allows gas (e.g., air) to traverse the mesh 370 while preventing liquid (e.g., wound exudate) from traversing the mesh 370. The mesh 370 can cover an additional filter 374 that is disposed across the collar 372 and the base 360 as shown in FIG. 13B. The mesh 370 can optionally have a convex or dome shape and can protrude away from the base 360 and the collar 370, as shown in FIG. 13B. The dome shape of the mesh 370 can provide air flow pathways at the periphery of the mesh 370 when the apex of the mesh 370 is submerged in or in contact with a liquid.

FIGS. 14A-14D illustrate a filter carrier 302I similar to the filter carrier 302H except as described differently below. The features of the filter earner 302I can be combined or included with the filter carrier 302H or any other embodiment discussed herein. The filter carrier 302H can include a pivoting snorkel 376. The pivoting snorkel 376 can be adapted to maintain a flow path between the canister 220 and the pump assembly 230 under different orientations of the canister 220. The snorkel 376 can be rotatably mounted on the base 360 of the filter carrier 302I. The snorkel 376 can include a counter weight 378 disposed at an end of the snorkel 376 as shown in FIG. 14B. The snorkel 376 can have an opening 380 disposed at an end opposite of the counter weight 378. The snorkel 376 can have an exit 382 that communicates with the internal space of the snorkel 376. The snorkel 376 can provide a flow path by which air in the canister 220 can flow toward the pump assembly 230 when the pump assembly 230 applies a negative pressure. When the pump assembly 230 applies negative pressure to the canister 220, air inside the canister 220 can enter the snorkel 376 through the opening 380 and flow out of the snorkel 376 through the exit 382.

FIG. 14C shows that the snorkel 376 can pivot when the canister 220 is oriented on its back so that the opening 380 of the snorkel 376 remains within the airspace that is above the liquid inside the canister 220. Gravity can pull the counterweight 378 to drive the snorkel 376 into the vertical orientation shown in FIG. 14C when the canister 220 is oriented on its back. When the canister 220 is upright, the snorkel 376 will have a substantially horizontal orientation as shown in FIG. 14D. FIG. 14B illustrates that the snorkel 376 can house an additional filter 374 (e.g., a polytetrafluoroethylene exclusion filter).

FIGS. 15A and 15B illustrate a filter carrier 302J similar to the filter carrier 302I except as described differently below. The features of the filter carrier 302J can be combined or included with the filter carrier 302I or any other embodiment discussed herein. The filter carrier 302J can form a unitary structure with the base portion 246 of the bulkhead 240, as shown in FIG. 15A. The filter carrier 302J can include one or more top baffles 384 that extend from the canister-side surface of the base portion 246. The one or more top baffles 384 can interlace with one or more corresponding bottom baffles 386 that extend from the interior surface of the canister 220. The top baffles 384 can extend only partially across the span between the interior surface of the canister 220 and the pump-side surface of the base portion 246. The bottom baffles 386 can extend only partially across the span between the pump-side surface of the base portion 246 and the interior surface of the canister 220. In this way, the interlacing baffles 384, 386 can provide a tortuous flow path between the interlacing walls of the baffles 384, 386 that allows fluid inside the canister 220 to access the central channel of the connector 242. However, the interlacing baffles 384, 386 reduce or prevent liquid inside the canister from splashing into the central lumen of the connector 242. The innermost top baffle 384 can house an additional filter 374. FIG. 15B illustrates that the interlacing baffles 384, 386 can be a plurality of substantially circular baffles that are concentrically arranged. As shown in FIGS. 15A and 15B, the interlacing baffles 384, 386 can be positioned near the inflow port 254 through which wound exudate can be drawn into the canister 220. In the illustrated embodiment, the interlacing baffles 384, 386 and the inflow port 254 are both located along a sagittal plane that passes through the hack surface 228 and the front surface 229 of the canister 220. In some arrangements, the interlacing baffles 384, 386 and the inflow port 254 can be positioned away from one another. For example, the interlacing baffles 384, 386 can be positioned near a corner formed by the right side and the front surface 229 of the canister 220B while the inflow port 254 is located near a corner formed by the left side and the rear surface 228 of the canister 220. In some embodiments, the interlacing baffles 384, 386 can be positioned away from the inflow port 254 to avoid frothing at the inflow port 254 from entering between the interlacing baffles 384, 386.

FIGS. 16A and 16B illustrate a filter carrier 302K similar to the filter carrier 302J except as described differently below. The features of the filter carrier 302K can be combined or included with the filter carrier 302J or any other embodiment discussed herein. The filter carrier 302K can attach to the base portion 246 of the bulkhead 240, as shown in FIG. 16A. The filter carrier 302K can include one or more top baffles 384 that extend from the canister-side surface of the filter carrier 302K. The one or more top baffles 384 can interlace with one or more corresponding bottom baffles 386 that extend from the interior surface of the canister 220. The top baffles 384 can extend only partially across the span between the interior surface of the canister 220 and the pump-side surface of the filter carrier 302K. The bottom baffles 386 can extend only partially across the span between the pump-side surface of filter carrier 302K and the interior surface of the canister 220. In this way, the interlacing baffles 384, 386 can provide a tortuous flow path between the interlacing walls of the baffles 384, 386 that allows fluid inside the canister 220 to access the central channel of the connector 242. However, the interlacing baffles 384, 386 can reduce or prevent liquid inside the canister 220 from splashing into the central lumen of the connector 242. The filter carrier 302K can house an additional filter 374. FIG. 16B illustrates that the interlacing baffles 384, 386 can be a plurality of substantially U-shaped baffles that are nested with one another. The interlacing baffles 384, 386 can be located near the inflow port 254 or away from the inflow port 254, as discussed above with regard to FIGS. 15A and 15B.

FIGS. 17A and 17B illustrate a filter carrier 302L similar to the filter carrier 302K except as described differently below. The features of the filter carrier 302L can be combined or included with the filter carrier 302K or any other embodiment discussed herein. The filter carrier 302L can have a central portion 320 having an inner rim 342 and an outer rim 343, as described previously with regard to FIG. 10A. The base portion 246 of the bulkhead 240 can have a nesting baffle 245 that extends from the pump-side surface of the base portion 246, as shown in FIG. 17A. The nesting baffle 245 can nest between the inner and outer rim 342, 343 of the central portion 320. The base portion 246 can have a floor 247 that extends between the lateral sides of the canister 220 and between the front and back faces of the canister 220, thereby substantially covering the mouth of the canister 220, as shown in FIG. 17B.

The base portion 246 can have an aperture 249 that communicates across the floor 247, thereby providing a flow path between the interior space of the canister 220 and the space between the base portion 246 and the cap portion 244 of the bulkhead 240. The aperture 249 can optionally be a slot that is substantially aligned with the left and right sides of the canister 220, as shown in FIG. 17B. In certain arrangements, the base portion 246 has an aperture 249a that is similar to the aperture 249 except that the aperture 249a is aligned substantially parallel with the front and back face of the canister, as shown in FIG. 17B. In certain arrangements, the aperture 249 has an orientation other than the being aligned substantially parallel with one of the sides of the canister 220. The floor 247 can be sloped so that liquid on the pump-side surface of the floor 247 drains toward the aperture 249. In some arrangements, the aperture 249 has a shape other than a linear slot (e.g., undulating slot, circular through hole). In some embodiments, the floor 247 has more than one aperture 249. The aperture 249 can be located near the inflow port 254 or away from the inflow port 254, as discussed above with regard to the filter stack 300 of FIG. 4.

The inner rim 342, the outer rim 343, and the nesting baffle 245 can be arranged to provide a flow path between the aperture 249 and the connector 242. The flow path can be more easily navigable by gas (e.g., air) than by liquid (e.g., wound exudate). As shown in FIG. 17A, the inner and outer rims 342, 343 can extend only partially toward the floor 247, leaving a gap that allows fluid to flow radially inward past the inner and outer rims 342, 343 and toward the connector 242. The nesting baffle 245 can extend only partially toward the canister-side surface of the central portion 320, leaving a gap that allows fluid to flow radially inward past the nesting baffle 245 and toward the connector 242. The inner rim 342, the outer rim 343, and the nesting baffle 245 can circumferentially surround the connector 242. The inner rim 342, the outer rim 343, and the nesting baffle 245 can create a flow path that allows the pump assembly 230 to apply negative pressure to the canister 220 while reducing or preventing wound exudate from contacting the connector 242 or a filter 374 housed within the filter carrier 302L. The filter 374 can be any filter mentioned herein (e.g., a shutoff an odor filter, an antibacterial filter, an exclusion filter).

Gas can easily flow radially inward past the inner rim 342, the outer rim 343, and the nesting baffle 245 to reach the connector 242, allowing the pump assembly 230 to draw out of the canister 220 and establish a negative pressure within the canister 220. When the canister 220 in an upright orientation (see FIG. 17A), liquid that flows from the canister 220 toward the connector 242 will encounter the nesting baffle 245 and tend to drain back into the canister through the aperture 249. As mentioned, in some arrangements the floor 247 can be sloped to facilitate liquid draining back toward the aperture 249. When the canister 220 is on its back (see FIG. 17B), the aperture 249 can be configured to provide a flow path that allows the air within the air pocket at the top of the canister to reach the connector 249. The inner rim 342, the outer rim 343, and the nesting baffle 245 can circumferentially surround the connector 242 so that liquid that flows from the canister 220 toward the connector 242 will encounter the inner rim 342, the outer rim 343, and the nesting baffle 245 when the canister 220 is oriented on its hack. Liquid that passes from the canister 220 through the aperture 249 will tend to drain hack into the canister through the aperture 249. As mentioned, in some arrangements the floor 247 can be sloped to facilitate liquid draining back toward the aperture 249.

Figure 17C:
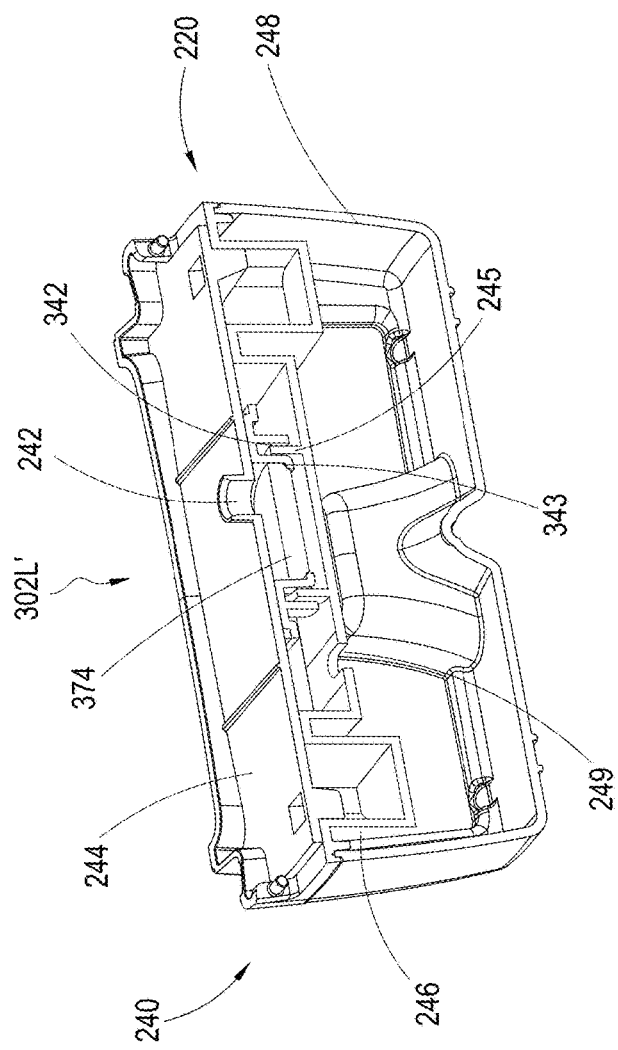
FIG. 17C is a partial front cross-sectional view of a filter carrier and canister.
Figure 17D:
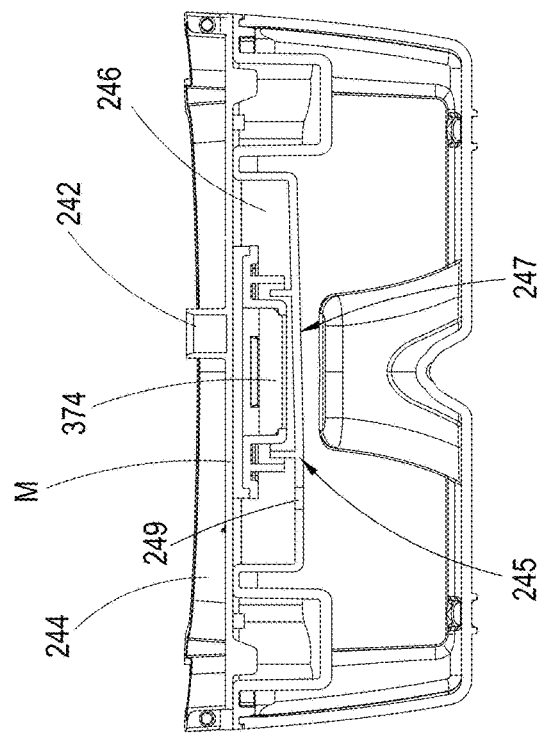
FIG. 17D is a front cross-sectional view of the filter carrier of FIG. 17C.

FIGS. 17C and 17D illustrate a filter carrier 302L' similar to the filter carrier 302L except as described differently below. The features of the filter carrier 302L' can be combined or included with the filter carrier 302L or any other embodiment discussed herein. As described above, the bulkhead 240 of the canister 220 includes the cap portion 244 and the base portion 246. The bulkhead 240 can be assembled onto the receptacle 248. In the illustrated embodiment, the filter carrier 302L' is disposed within the space between the cap portion 244 and the base portion 246. The cap portion 244 seals the mouth of the receptacle 248. As discussed, the floor 247 of the cap portion 244 has an aperture 249 that allows gas (e.g., air) within the receptacle 248 to flow into the space between the cap portion 244 and the base portion 246 to reach the connector 242. The filter carrier 302L' can include a manifold M (shown best in FIG. 4). The manifold M can be adapted to distribute over the transverse top surface of the filter stack the negative pressure that is supplied through the connector 242. The manifold M can be surrounded circumferentially by a seal to fluidically isolate the connector 242 from the space between the cap portion 244 and the base portion 246. The filter carrier 302L' can be arranged such that gas cannot access the connector 242 without passing first through the filter 347.

As discussed above, the floor 247 of the base portion 246 can include an aperture 249 that communicates between the interior space of the receptacle 248 and the interior space of the bulkhead 240. The aperture 249 provides a flow path across the floor 247. In the illustrated embodiment, the floor 247 has a single aperture 249. The floor 247 is sloped downward toward the aperture 249 so that liquid within the space between the cap portion 244 and the base portion 246 drains back to the aperture 249 to return to the interior space of the receptacle 248.

The base portion 246 of the bulkhead 240 can have a nesting baffle 245 that extends from the pump-side surface of the base portion 246 and nests between the inner and outer rim 342, 343 of the central portion 320, as described above with regard to FIGS. 17A and 17B. The inner rim 342, the outer rim 343, and the nesting baffle 245 can be arranged to provide a flow path between the aperture 249 and the connector 242. The flow path can be more easily navigable by gas (e.g., air) than by liquid (e.g., wound exudate), as described above. The inner rim 342, the outer rim 343, and the nesting baffle 245 can create a flow path that allows the pump assembly 230 to apply negative pressure to the canister 220 while reducing or preventing wound exudate from contacting the connector 242 or a filter 374 housed within the filter carrier 302L'. The filter 374 can be any filter mentioned herein (e.g., a shutoff an odor filter, an antibacterial filter, an exclusion filter). As discussed previously, gas can flow radially inward past the inner rim 342, the outer rim 343, and the nesting baffle 245 to reach the connector 242. Liquid that passes through the aperture 249 to reach the interior space of the bulkhead 240 will encounter the nesting baffle 245 and tend to drain back into the canister through the aperture 249. As mentioned, in some arrangements the floor 247 can be sloped to facilitate liquid draining back toward the aperture 249. The inner rim 342, the outer rim 343, and the nesting baffle 245 can circumferentially surround the connector 242, as described previously with regard to FIGS. 17A and 17B. The inner rim 342, the outer rim 343, and the nesting baffle 245 can be concentric with one another. In this way, the inner rim 342, the outer rim 343, and the nesting baffle 245 can form a plurality of concentric baffles.

Figure 18B:
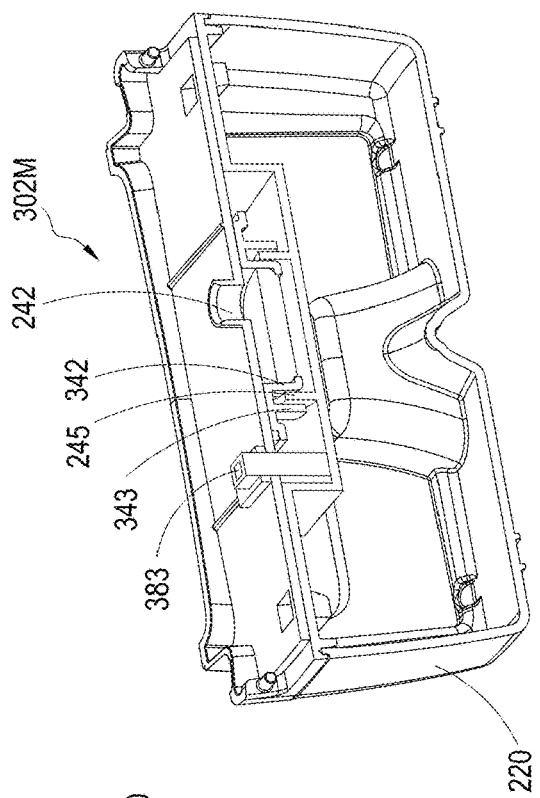
FIG. 18B is a front cross-sectional view of the filter carrier and canister of FIG. 18A.
Figure 18C:
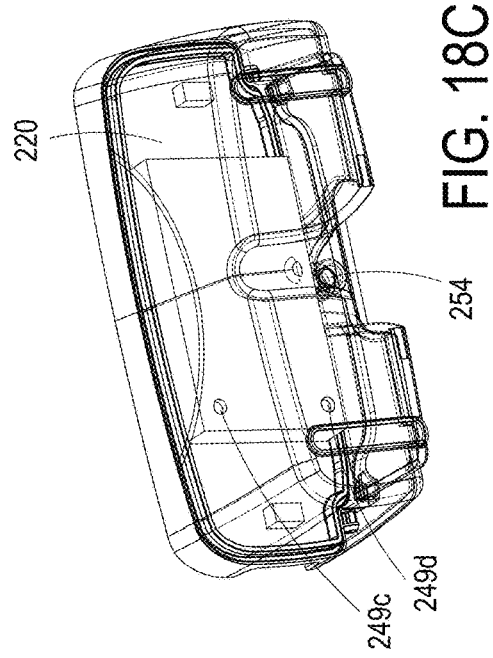
FIG. 18C is a bottom view of the filter carrier of FIG. 18A when the canister is oriented on its back.
Figure 18A:
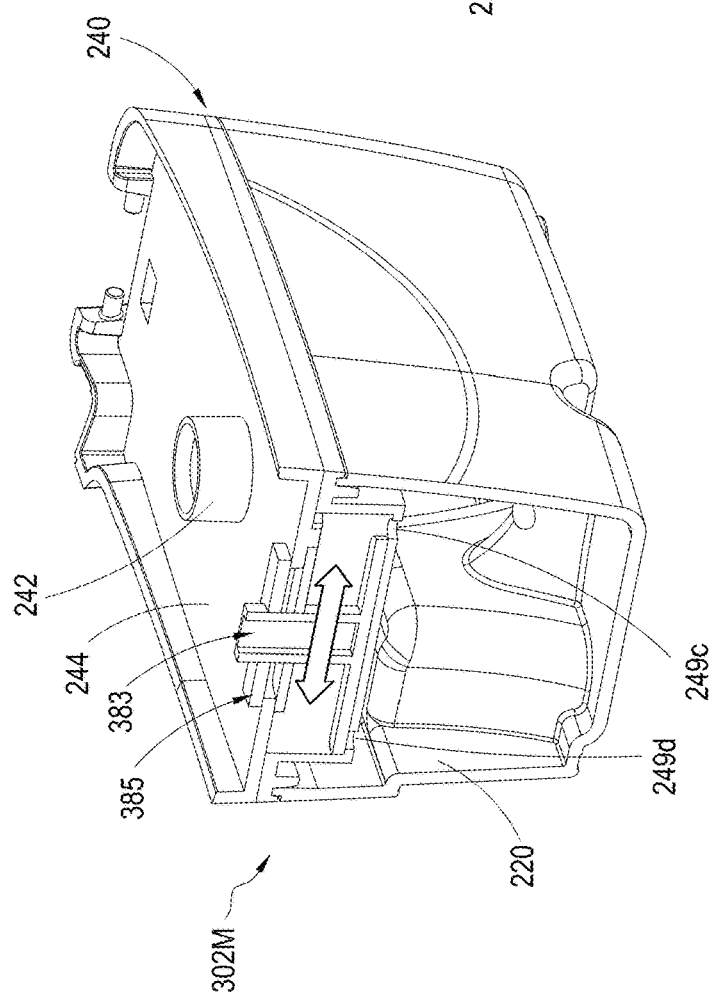
FIG. 18A is a side cross-sectional view of a filter carrier and canister.

FIGS. 18A-18C illustrate a filter carrier 302M similar to the filter carrier 302L except as described differently below. The features of the filter carrier 302M can be combined or included with the filter carrier 302L or any other embodiment discussed herein. The filter carrier 302M can include a pair of spaced apart apertures 249c, 249d that are similar to the aperture 249 previously described. The apertures 249c, 249d can be circular through holes and can be substantially aligned with one another along a line that is substantially perpendicular to the front of the canister 220, as shown in FIG. 18C. The front aperture 249c can be disposed between the front surface of the canister 220 and the rear aperture 249d. The rear aperture 249d can be disposed between the front surface of the canister 220 and the front aperture 249c. The filter carrier 302M can include a moveable arm 383 that can move between a rearward position and a frontward position, as indicated in FIG. 18A. The rear aperture 249d can be blocked by the moveable arm 383 when the movable are 383 is in the rearward position. The front aperture 249c can be blocked by the moveable arm 383 when the movable arm 383 is in the frontward position. The position of the moveable arm 383 can be operated and controlled by a solenoid or a motor in the pump housing. An elastomeric seal 385 can provide a seal between the moveable arm 383 and the cap portion 244 of the bulkhead 240, as shown in FIG. 18A. Referring to FIG. 18B, the filter carrier 302M can include an inner rim 342, an outer rim 343, and a nesting baffle 245 that are arranged to create a tortuous flow path between the canister 220 and the connector 242, as described previously with regard to the filter carrier 302L shown in FIG. 17A. The apertures 249c, d can be located near the inflow port 254 or away from the inflow port 254, as discussed above with regard to FIGS. 17A and 17B.

FIGS. 19A and 199 illustrate the filter carrier 302M shown in FIGS. 18A and 18B. FIG. 19A shows operation of the filter carrier 302M when the canister 220 is positioned on its back, with a back surface 228 of the canister 220 facing down and a front surface 229 of the canister 220 facing up. FIG. 19B shows operation of the filter carrier 302M when the canister 220 is positioned on its front, with a back surface 228 of the canister 220 facing up and a front surface 229 of the canister 220 facing down. As shown in FIG. 19A, the movable arm 383 can be moved to cover the rear aperture 249d when the canister 220 is positioned on its back, thereby leaving open the front aperture 249c and providing a flow path between the canister 220 and the connector 224, as described previously. As shown in FIG. 19B, the movable arm 383 can be moved to cover the front aperture 249c when the canister 220 is positioned on its front, thereby leaving open the front aperture 249d and providing a flow path between the canister 220 and the connector 224, as described previously. The pump assembly 230 can include a sensor (e.g., gyroscope) to allow the pump assembly 230 to sense the orientation of the canister 220. The pump assembly 230 can control or operate a motor coupled to the moveable arm 383 to move the moveable arm 383 to the forward or rearward position based on the determination of the canister orientation.

FIGS. 20A-20D illustrate a filter carrier 302N similar to the filter carrier 302M except as described differently below. The features of the filter carrier 302N can be combined or included with the filter carrier 302M or any other embodiment discussed herein. The filter carrier 302N can include a float 390 that is connected to the central portion 320 by a flexible tube 392. The float 390 can have an opening 394 that is in fluid communication with the tube 392, as shown in FIG. 20B. The float 390 can include a keel 396 that keeps the opening 394 oriented to face upward relative to gravity. FIG. 20C illustrates the canister 220 when the canister 220 is in an upright position. As shown in FIG. 20C, the keel 396 can pivot the float 390 to keep the opening 394 directed upward to provide a flow path for air within the canister 220 to reach the connector 242 by flowing through the tube 392. FIG. 20D illustrates the canister 220 is positioned on its back. As shown in FIG. 20D, the float 390 can pivot to keep the opening 394 directed up, thereby providing a flow path for air within the air pocket inside the canister 220 to flow through the tube 392 to reach the connector 242.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc, may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A canister for a negative pressure wound therapy apparatus comprising:
  a receptacle having a space therein configured to be placed in fluid communication with a dressing covering a wound, the receptacle being configured and to receive an exudate from the wound;
  an outlet opening configured to be in fluid communication with a pump assembly; and
  a filter assembly disposed between the receptacle and the outlet opening and defining a flow path therebetween, the filter assembly comprising:
    a central portion comprising a longitudinal wall, a support wall, and an inner rim, the inner rim circumferentially surrounding a central opening and being connected to the longitudinal wall by the support wall; and a guard attached to a canister side surface of the support wall and extending radially across the central opening.

2. The canister of claim 1, further comprising a filter selected from the group consisting of a hydrophobic filter, a hydrophilic filter, an exclusion filter, an antibacterial filter, and an odor filter.

3. The canister of claim 1, wherein the guard comprises a flange extending from a pump-side surface of the guard, the flange being disposed radially outward of the inner rim.

4. The canister of claim 3, wherein the flange of the guard comprises a notched section that leaves an entrance gap that provides fluid communication between the receptacle and the flow path.

5. The canister of claim 4, wherein the inner rim comprises a notched portion forming an exit gap between the inner rim and the guard that provides fluid communication between the outlet opening and the flow path.

6. The canister of claim 5, wherein the flange of the guard comprises a notched section that leaves an entrance gap that provides fluid communication between the receptacle and the flow path and wherein the notched section is circumferentially opposite of the notched portion.

7. The canister of claim 6, wherein the guard further comprises one or more hurdles that extend from the pump-side surface of the guard, the hurdles spanning from the flange to the inner rim.

8. The canister of claim 7, wherein at least one of the one or more hurdles extends only partially between the flange and the support wall.

9. The canister of claim 1, wherein the guard is ultrasonically welded to the support wall.

10. The canister of claim 1, wherein the guard is positioned substantially perpendicular to a longitudinal axis of the central opening.

11. The canister of claim 1, wherein the inner rim comprises an area of reduced height that forms a notch.

12. The canister of claim 1, wherein the guard comprises a flange extending from a pump-side surface of the guard and wherein the guard and the support wall form a channel therebetween, the channel bounded laterally by the inner rim and the flange and bounded axially by the support wall and the guard.

13. A canister for a negative pressure wound therapy apparatus comprising:
a receptacle in fluid communication with a dressing covering a wound, the receptacle being configured to receive an exudate from the wound;
a connector in fluid communication with a pump assembly; and
a filter assembly disposed between the receptacle and the connector and defining a flow path therebetween, the filter assembly comprising:
a central portion comprising a longitudinal wall, a shelf, and an inner rim, the inner rim circumferentially surrounding a central opening and being connected to the longitudinal wall by the shelf;
a guard attached to a canister side surface of the shelf and extending radially across the central opening.

14. The canister of claim 13, wherein the guard comprises a flange extending from a pump-side surface of the guard, the flange being disposed radially outward of the inner rim, a notched section of the flange leaving an entrance gap between the flange and the shelf that provides fluid communication between the receptacle and the flow path.

15. The canister of claim 14, wherein the inner rim comprises a notched portion forming an exit gap between the inner rim and the guard that provides fluid communication between the connector and the flow path.

16. The canister of claim 15, wherein the notched section is circumferentially opposite of the notched portion.

17. The canister of claim 16, wherein the guard further comprises one or more hurdles that extend from the pump-side surface of the guard, the hurdles spanning from the flange to the inner rim.

18. The canister of claim 17, wherein at least one of the one or more hurdles extends only partially between the flange and the shelf.

19. The canister of claim 13, wherein the guard is ultrasonically welded to the shelf.

20. The canister of claim 13, further comprising a filter selected from the group consisting of a hydrophobic filter, a hydrophilic filter, an exclusion filter, an antibacterial filter, and an odor filter.

21. The canister of claim 13, wherein the guard is positioned substantially perpendicular to a longitudinal axis of the central opening.

22. The canister of claim 13, wherein the guard comprises a flange that circumferentially surrounds the inner rim.

23. The canister of claim 13, wherein the inner rim comprises an area of reduced height that forms a notch.

24. The canister of claim 13, wherein the guard and the shelf form a channel therebetween, the channel bounded laterally by the inner rim and a flange extending from a pump-side surface of the guard and bounded axially by the shelf and the guard.

\* \* \* \* \*